(12) United States Patent
Valen

(10) Patent No.: US 9,238,047 B1
(45) Date of Patent: Jan. 19, 2016

(54) FLUORAPATITE NANO-CRYSTALLINE COATED NON-CERAMIC HYDROPHILIC HYDROXYLAPATITE BONE GRAFTING COMPOSITIONS AND METHODS FOR PROMOTING BONE REGENERATION

(71) Applicant: Maurice Valen, Holliswood, NY (US)

(72) Inventor: Maurice Valen, Holliswood, NY (US)

( * ) Notice: Subject to any disclaimer, the term of this patent is extended or adjusted under 35 U.S.C. 154(b) by 0 days.

(21) Appl. No.: 13/738,307

(22) Filed: Jan. 10, 2013

(51) Int. Cl.
*A61K 33/42* (2006.01)
*A61K 9/16* (2006.01)
*B65B 5/00* (2006.01)

(52) U.S. Cl.
CPC .. *A61K 33/42* (2013.01); *B65B 5/00* (2013.01)

(58) Field of Classification Search
None
See application file for complete search history.

(56) References Cited

U.S. PATENT DOCUMENTS 4,904,257 A * 2/1990 Mori et al. ............... 106/161.1

OTHER PUBLICATIONS

Kim et al., "Sol-Gel Preparation and Properties of Fluoride-Substituted Hydroxyapatite Powders", 2004, J. Am. Ceram. Soc., vol. 87, No. 10, pp. 1939-1944.*

* cited by examiner

*Primary Examiner* — Michael B Pallay
(74) *Attorney, Agent, or Firm* — Maxine L. Barasch; Keohane & D'Alessandro, PLLC

(57) ABSTRACT

Bone graft compositions and methods are provided for promoting cellular recruitment bone regeneration. The novel bone graft includes at least one of: fluorapatite nano-crystalline coated non-ceramic hydrophilic hydroxylapatite crystals; and a combination of fluorapatite nano-crystalline coated non-ceramic hydrophilic hydroxylapatite crystals and fluorapatite nano-crystalline coated hydroxylapatite crystal clusters. Methods include treating cells at a bone defect site with the novel bone graft, wherein fluorapatite crystallites from the fluorapatite nano-crystalline coating immediately and continuously release fluorapatite to the cellular environment over the course of treating the cells. The compositions and methods promote cell differentiation, migration, and proliferation. Through the use of compositions and methods provided herein, inhibition of the migration of connective tissue and epithelial cells to bone defect sites is realized for better bone restoration by osteoblast cells. Moreover, inhibition of inflammatory cells and bacteria at the surgical site are realized, further enhancing bone restoration.

23 Claims, 19 Drawing Sheets
(18 of 19 Drawing Sheet(s) Filed in Color)

Figure 10

FLUORAPATITE NANO-CRYSTALLINE COATED NON-CERAMIC HYDROPHILIC HYDROXYLAPATITE BONE GRAFTING COMPOSITIONS AND METHODS FOR PROMOTING BONE REGENERATION

CROSS REFERENCE

Not applicable.

BACKGROUND

Metal implants cannot be placed in deficient bone sites without the use of guided bone grafting regeneration procedures. Such procedures are clinically necessary in osseous defects for implant installation in orthopedics and dentistry. Grafting materials that may be used for guided bone regeneration include autograft bone, allograft bone and synthetic bioactive resorbable crystals, having physicochemical properties and biologic resorption rates to human bone. However, use of ceramic hydroxyapatite granules, bovine ceramic granules, tricalcium phosphate ceramic granules, glass and/or plastic granules results in negative systemic consequences further compromising the patient's immune system due to lack of resorption and physicochemical dissimilarities to human bone. Such materials are all considered non-resorbing filler materials which do not turn into bone, or resorb, due to their high mechanical properties and chemical dissimilarities to human bone.

Various titanium implant modalities (orthopedic or dental) have been developed in recent years with a variety of modified chemical surfaces, claiming biological protein attachment, cell attachment, and cell proliferation on their surfaces. These include ceramic hydroxyapatite coating, or calcium phosphate ceramic coating and titanium surface coating. Acid processing with fluoride surface treatment of implants and fluoride surface painting procedures have heretofore not provided any beneficial results, noting bone breakdown.

It has been reported that osteoblast proliferation and differentiation, as detected by alkaline phosphatase biochemical osteoblast marker activity, may be facilitated through free fluoride dried on the surfaces of implantable materials and devices. Free fluoride studies have been carried out for many years and have found that free fluoride may activate rapid and uncontrolled dissolution of bone, which may improve the rate of sporadic mineral apposition; however, the concentrations of free fluoride used in these studies vary considerably depending on the research equipment and testing methods used to evaluate the results. This wide range of free fluoride has not been narrowed down to an optimal free fluoride concentration by a controlled delivery mechanism with beneficial results, and without the consequences of bone necrosis due to the free fluoride's acidic poisonous nature and rapid immediate bone resorption.

There have been numerous studies of free fluoride clinical applications on the surface of human enamel carried out from the perspective of preventing caries. The concept of using sodium fluoride (NaF) to prevent caries emerged on the notion that free fluoride would either be "firmly bound" or "loosely attached" to enamel surface. This is based on early reports from in vitro studies on necrotic human tooth enamel surfaces, and clinical studies on human tooth enamel. This concept did not materialize, but instead resulted in deleterious outcomes and host bone necrosis. Hypothetically, these are alkali-"insoluble" and alkali-soluble fluorides, respectively, on various surfaces, with regard to solubility, using potassium hydroxide and with sodium-fluoride applications. Consecutive studies focused on the dissolution and mobility of free fluoride after topical applications in human and bovine tooth enamel surfaces. However, results failed to show controlled distribution of fluoride and any binding capacity to enamel surfaces. Therefore, no benefit was achieved by using free fluoride due to its instantaneous release to the cellular environment.

In other reports, mouse stem cells and osteoblast-like ROS cells responded to similar, or slightly lower, ranges of free fluoride substitution and showed good proliferation. Studies on epithelial cells in vitro focused on the presence of minute quantities of free fluoride from 5 to 50 µm (0.095-0.95 ppm F) in the culture medium, which promoted cell proliferation of human gingival epithelial cells (HGEC) and human epidermal cells (HaCaT) after 48-hour exposure. A significant difference was reported for proliferation of both cell types. The presence of "minute quantities" of free fluoride led to the production of fibronectin and laminin-5, which play a major role in cell adhesion and proliferation.

In view of the foregoing, there exists a need for bone graft and method of use that addresses the deficiencies of the related art for quicker and safer bone formation.

SUMMARY

Novel compositions and methods are provided herein for promoting bone cell recruitment, differentiation, migration, and proliferation, in addition to osteogenesis, and bone regeneration at (e.g., without limitation, dental, periodontal, and orthopedic) defect sites by hydrophilic bone grafting compositions. The inventive chemotactic methods and compositions demonstrate benefits including but not limited to connective tissue control and epithelial cell inhibition. Methods include promoting bone regeneration, by recruitment of osteoprogenitor cells/undifferentiated stem cells to a bone defect site for differentiation, migration, and proliferation as osteoblasts and osteoclasts, etc.

Embodiments of the present invention provide a bone graft composition comprising one of: fluorapatite nano-crystalline coated hydroxylapatite crystals; and a combination of fluorapatite nano-crystalline coated hydroxylapatite crystals and fluorapatite nano-crystalline coated hydroxylapatite crystal clusters. The fluorapatite nano-crystalline coated hydroxylapatite crystals comprise a fluorapatite nano-crystalline coating chemically bound to a surface of non-ceramic hydrophilic hydroxylapatite crystals. The fluorapatite nano-crystalline coated hydroxylapatite crystal clusters comprise a fluorapatite nano-crystalline coating chemically bound to a surface of non-ceramic hydrophilic hydroxylapatite crystal clusters. The bone graft releases fluorapatite to a cellular environment of the plurality of cells in a time-release mechanism. In some embodiments of the invention, the bone graft is deliverable as sterilized crystals/crystal clusters, a putty, a solid adaptable shape, or a bioactive interface.

Embodiments of the present invention provide a method for promoting bone regeneration at a bone defect site, the method comprising: treating a plurality of cells with a bone graft comprising one of:
   fluorapatite nano-crystalline coated hydroxylapatite crystals; and
   fluorapatite nano-crystalline coated hydroxylapatite crystals and fluorapatite nano-crystalline coated hydroxylapatite crystal clusters.

The fluorapatite nano-crystalline coated hydroxylapatite crystals comprise a fluorapatite nano-crystalline coating chemically bound to a surface of non-ceramic hydrophilic hydroxylapatite crystals. The fluorapatite nano-crystalline coated hydroxylapatite crystal clusters comprise a fluorapatite nano-crystalline coating chemically bound to a surface of non-ceramic hydrophilic hydroxylapatite crystal clusters. The bone graft releases fluorapatite to a cellular environment of the plurality of cells in a time-release mechanism. In some embodiments of the invention, the bone graft is delivered to the plurality of cells as sterilized crystals/crystal clusters, a putty, a pre-formed solid adaptable shape, or a bioactive interface.

In some embodiments, the hydroxylapatite crystals and/or hydroxylapatite crystal clusters of the bone graft are of a substantially homogeneous size. In some embodiments, the crystals and/or hydroxylapatite crystal clusters of the bone graft are of a substantially non-homogeneous size.

In some embodiments, the method for preparing the fluorapatite nano-crystalline coated hydroxylapatite bone graft, comprises: sieving at least one of non-ceramic hydrophilic hydroxylapatite crystals and non-ceramic hydrophilic hydroxylapatite crystal clusters to achieve a desired size; blending the sieved at least one of non-ceramic hydrophilic hydroxylapatite crystals and non-ceramic hydrophilic hydroxylapatite crystal clusters; immersing the blended at least one of non-ceramic hydrophilic hydroxylapatite crystals and non-ceramic hydrophilic hydroxylapatite crystal clusters in a solution comprising sodium fluoride to form a fluorapatite nano-crystalline coated hydroxylapatite bone graft; removing the fluorapatite nano-crystalline coated hydroxylapatite bone graft from the solution; washing the fluorapatite nano-crystalline coated hydroxylapatite bone graft; and drying the fluorapatite nano-crystalline coated hydroxylapatite bone graft. In some embodiments, the bone graft is further prepared for delivery to the defect site as a sterilized crystal composition, a putty, a solid adaptable shape, or a bioactive interface of an implantable device.

A better understanding of the invention will be obtained by reference to the following description and the accompanying drawings, which set forth exemplary embodiments in which the principles of the invention are utilized.

DRAWINGS

The patent or application file contains at least one drawing executed in color. Copies of this patent or patent application publication with color drawing(s) will be provided by the Office upon request and payment of the necessary fee.

These and other features of this invention will be more readily understood from the following detailed description of the various aspects of the invention taken in conjunction with the accompanying drawings in which:

FIG. 1 shows a scanning electron micrograph (SEM) image of a cluster of non-ceramic synthetic bioactive resorbable hydroxylapatite crystals resembling the physicochemical properties of human trabecular bone mineral similar to biologic crystals with the formula $Ca_5(PO_4)_3(OH)$, without the fluorapatite nano-crystalline coating.

FIG. 2 provides a graphical representation of quantitative gradual release from the novel bone graft over time of fluorapatite into the cellular environment of cells in culture medium.

Figure 4:
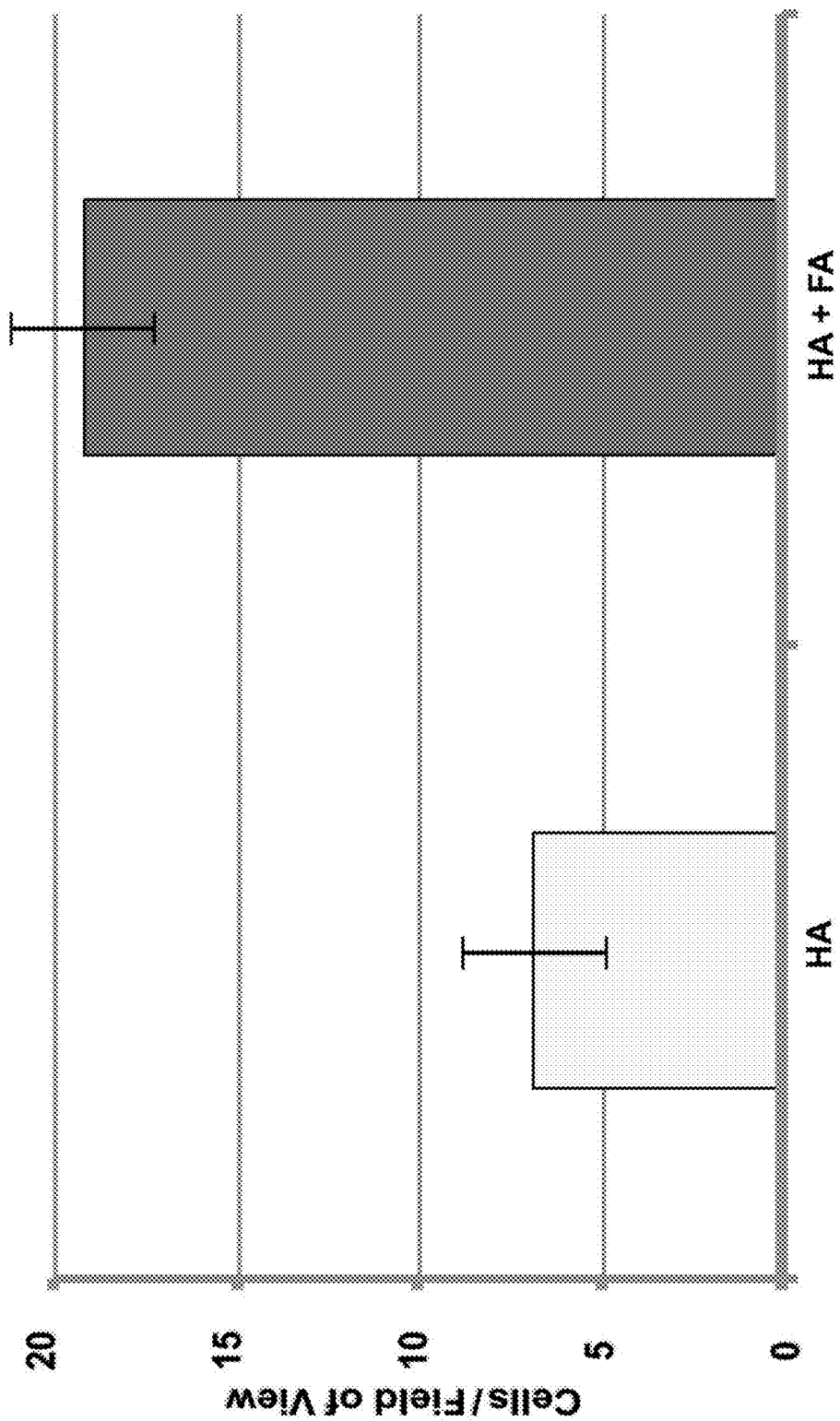

FIG. 4 provides a graphical representation of osteoblast proliferation with treatment by non-fluoridated hydroxylapatite crystals comparing to treatment with the novel bone graft of the present invention (hydroxylapatite comprising fluorapatite nano-crystalline coating).

Figure 5:
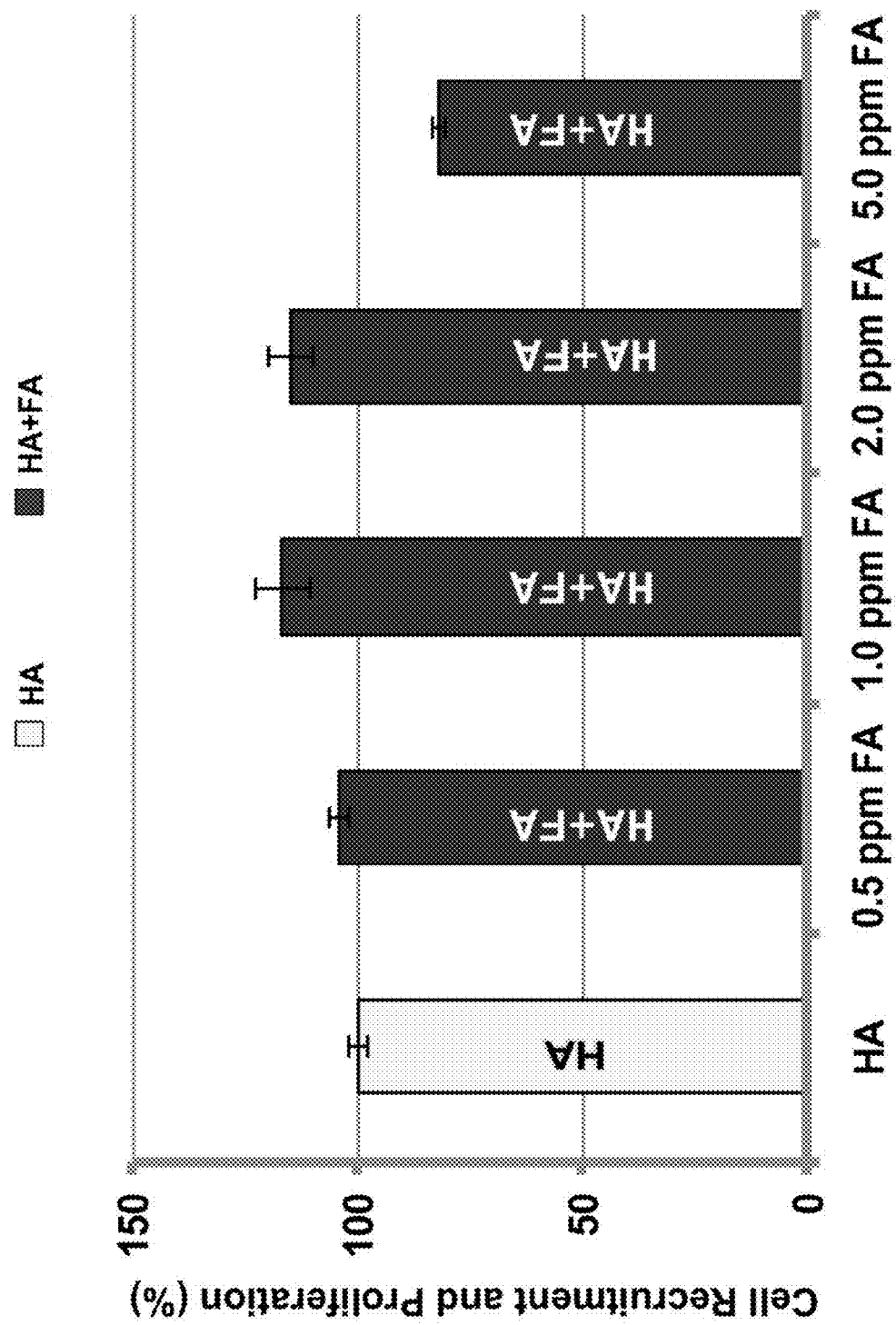

FIG. 5 provides a graphical representation of the effects of released fluorapatite on cell recruitment and proliferation at varying concentrations of fluorapatite.

Figure 6:
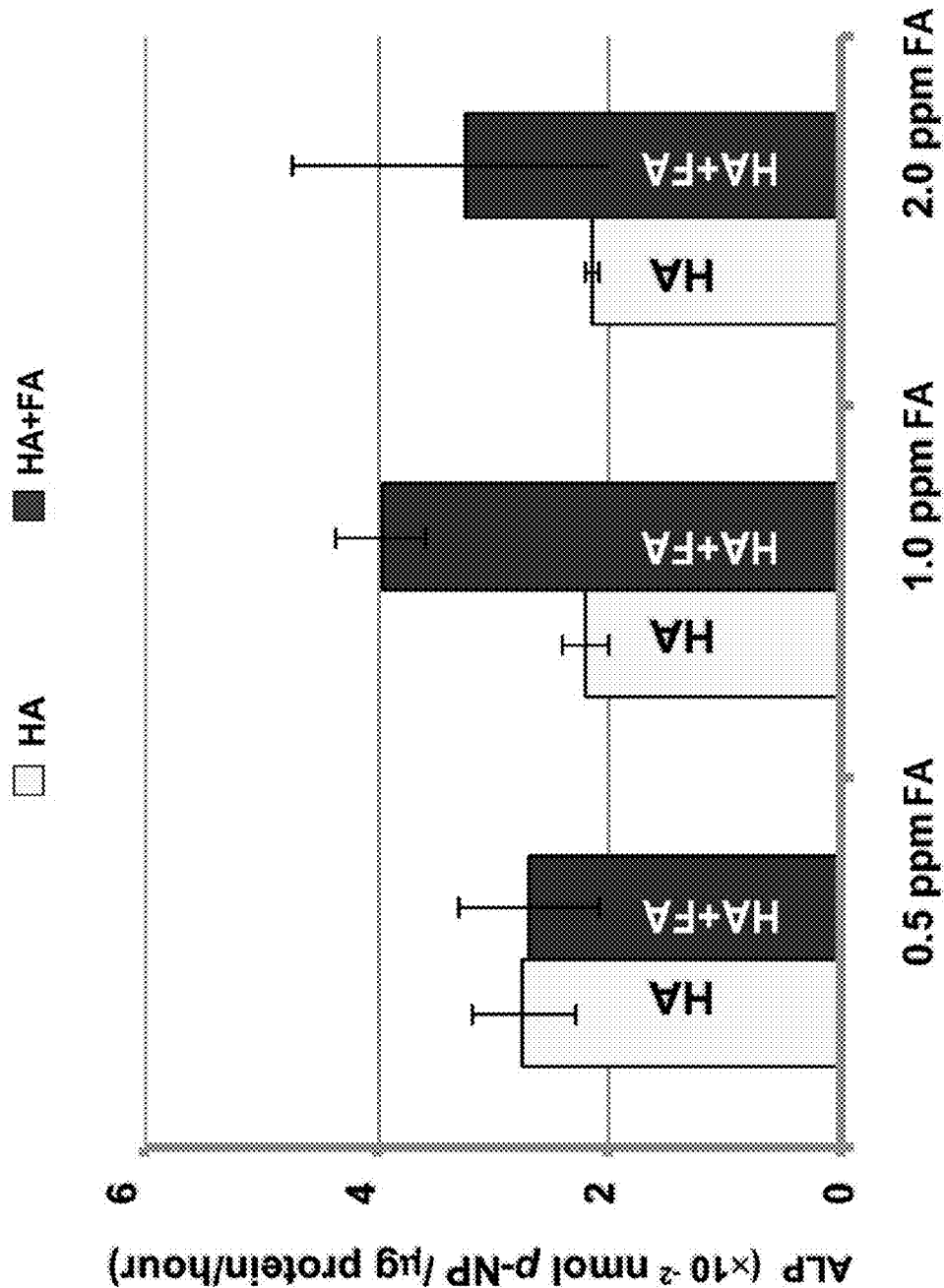

FIG. 6 provides a graphical representation of the effects of released fluorapatite, at varying concentrations, from the novel bone graft, as compared to non-coated hydroxylapatite, by alkaline phosphatase activity in MG-63 osteoblast cells.

Figure 7:
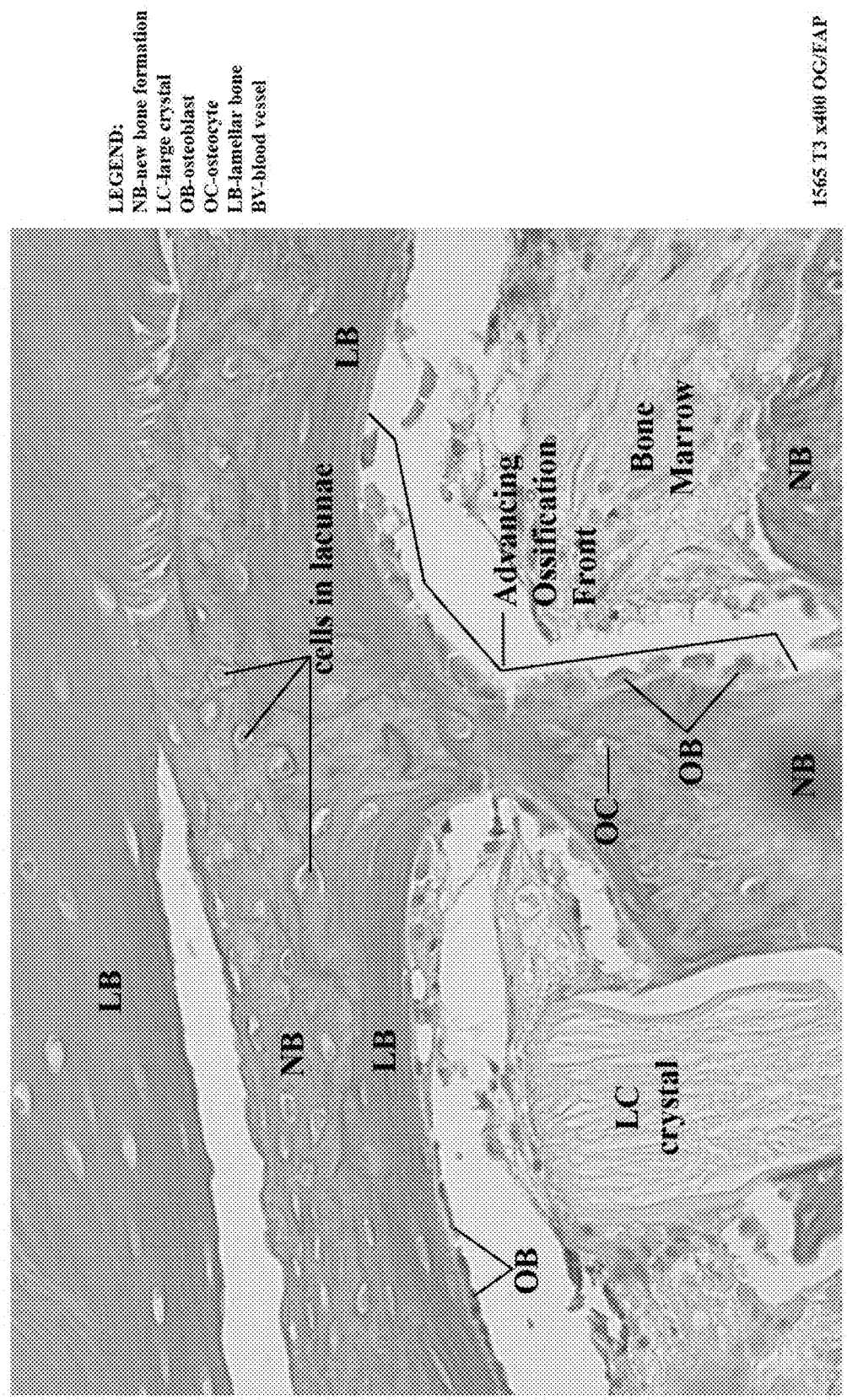

FIG. 7 provides animal histology in vivo, showing an advancing ossification front by osteoblasts laying done new bone, due to fluorapatite released from the novel bone graft, for lamellar bone formation (LB), showing mature bone with osteoblast cells in their lacunae (osteocyte) at twice the rate of normal bone formation and crystal resorption (normal bone regeneration takes approximately 142 days).

Figure 8:
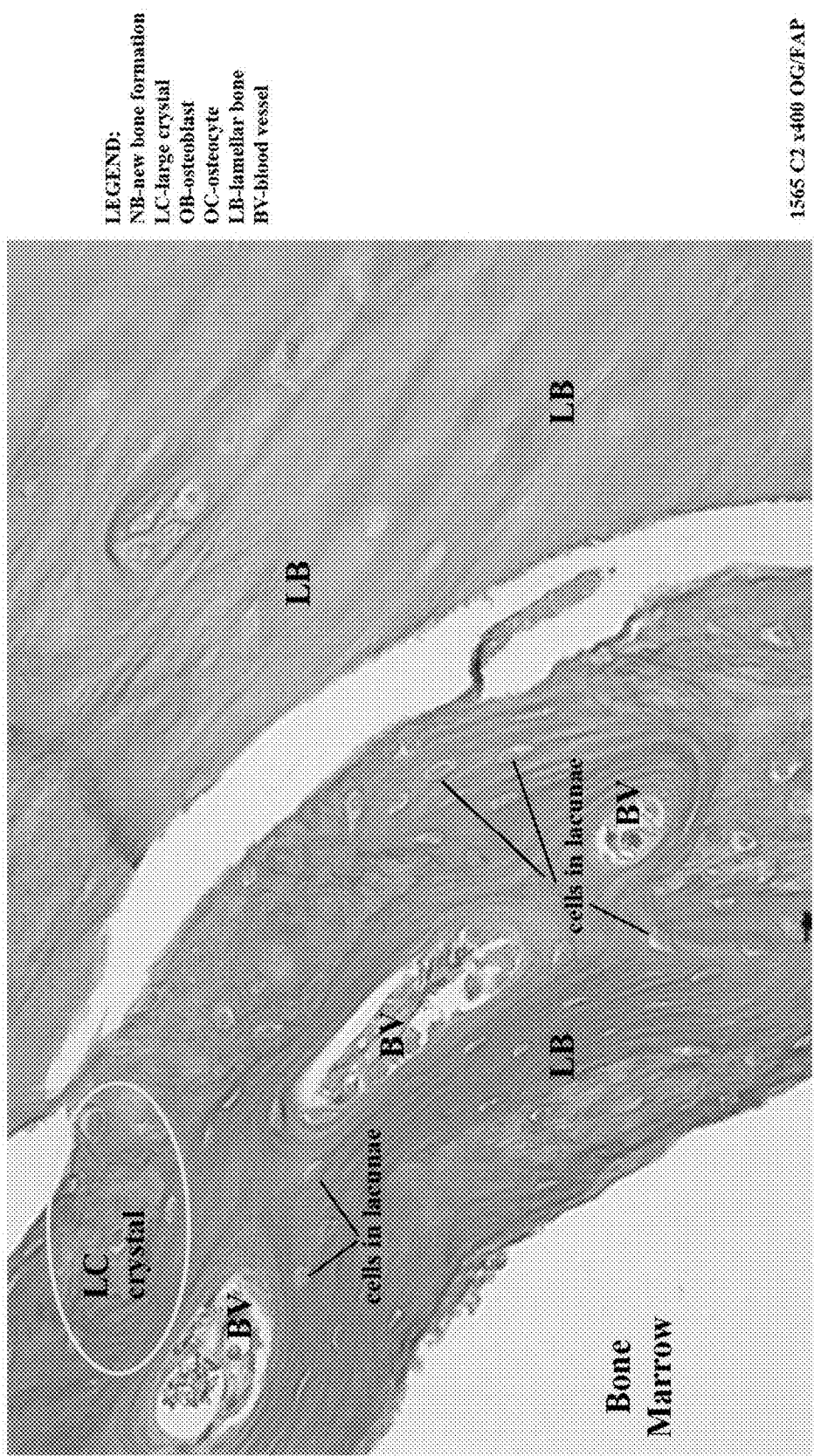

FIG. 8 provides animal histology in vivo, showing large hydroxylapatite crystals coated with the fluorapatite nano-crystalline coating in their last phase of resorption; noting an osteocyte within the fluorapatite nano-crystalline coated hydroxylapatite crystal, which is surrounded by mature bone while undergoing a metamorphic conversion to physiologic bone (yellow notation).

Figure 9:
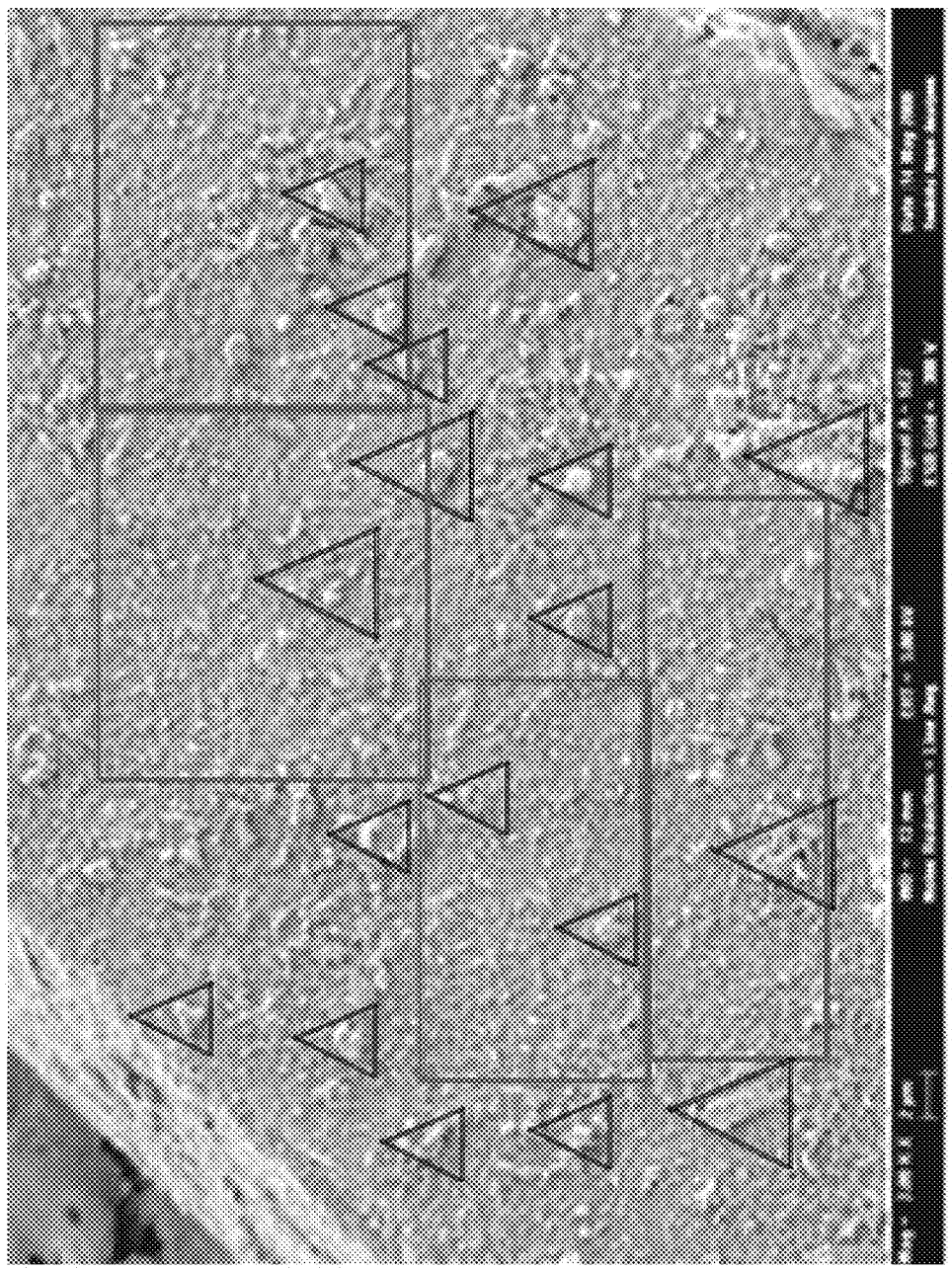

FIG. 9 shows a close up at ×2000 scanning electron micrograph image of an embodiment of the novel bone graft comprising a large hydroxylapatite crystal coated with the fluorapatite nano-crystalline coating.

Figure 10:
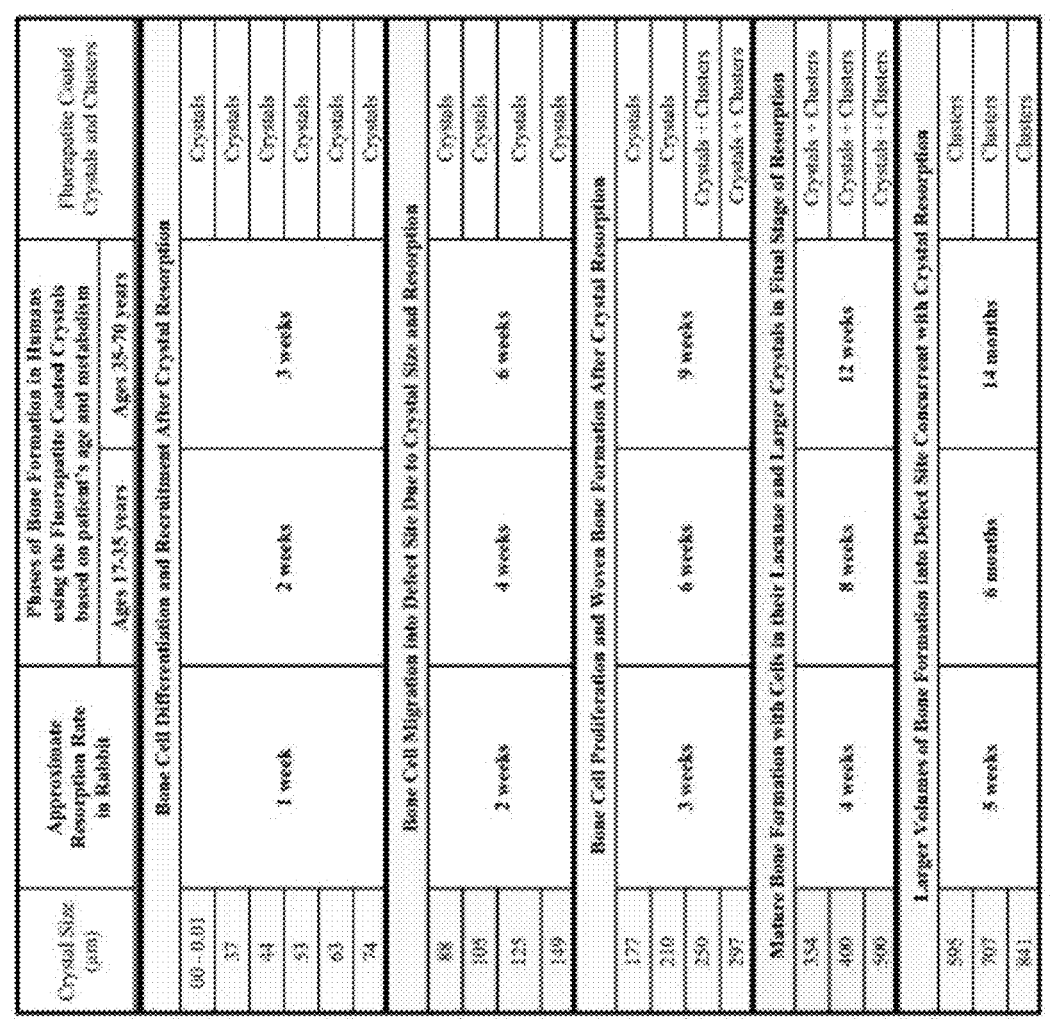

FIG. 10 shows a chart of fluorapatite nano-crystalline coated hydroxylapatite crystal size vs. resorption rate by histologic evaluation and bone formation at different time periods, comparing animals to humans.

Figure 11:
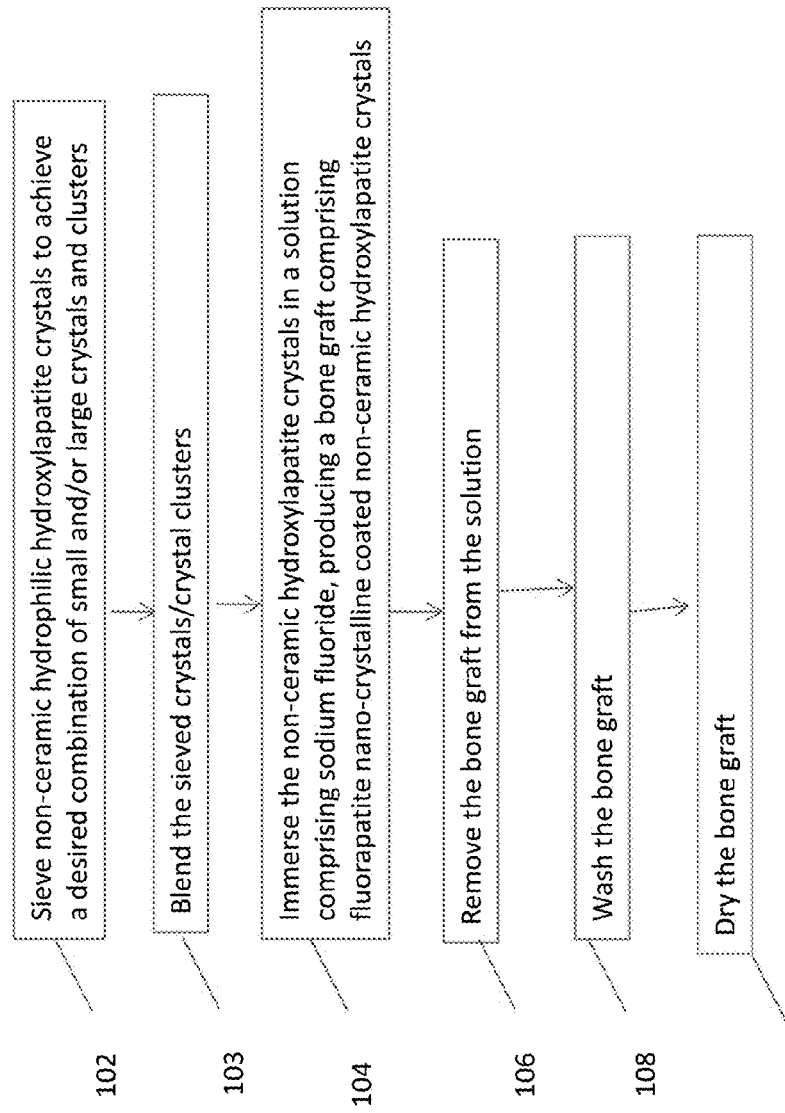

FIG. 11 shows a block diagram of a method for preparing the novel bone graft.

Figure 12:
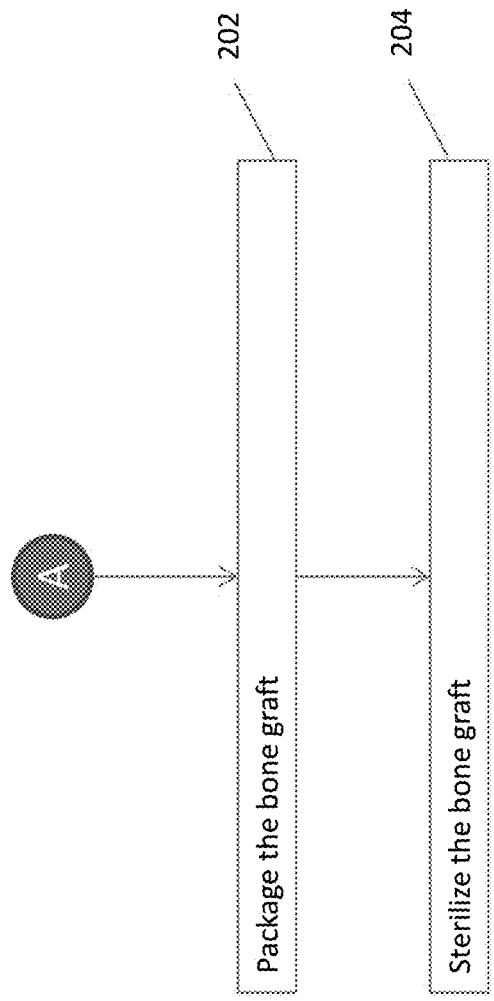

FIG. 12 shows a block diagram for preparing the bone graft as a sterilized crystal composition for end use.

Figure 13:
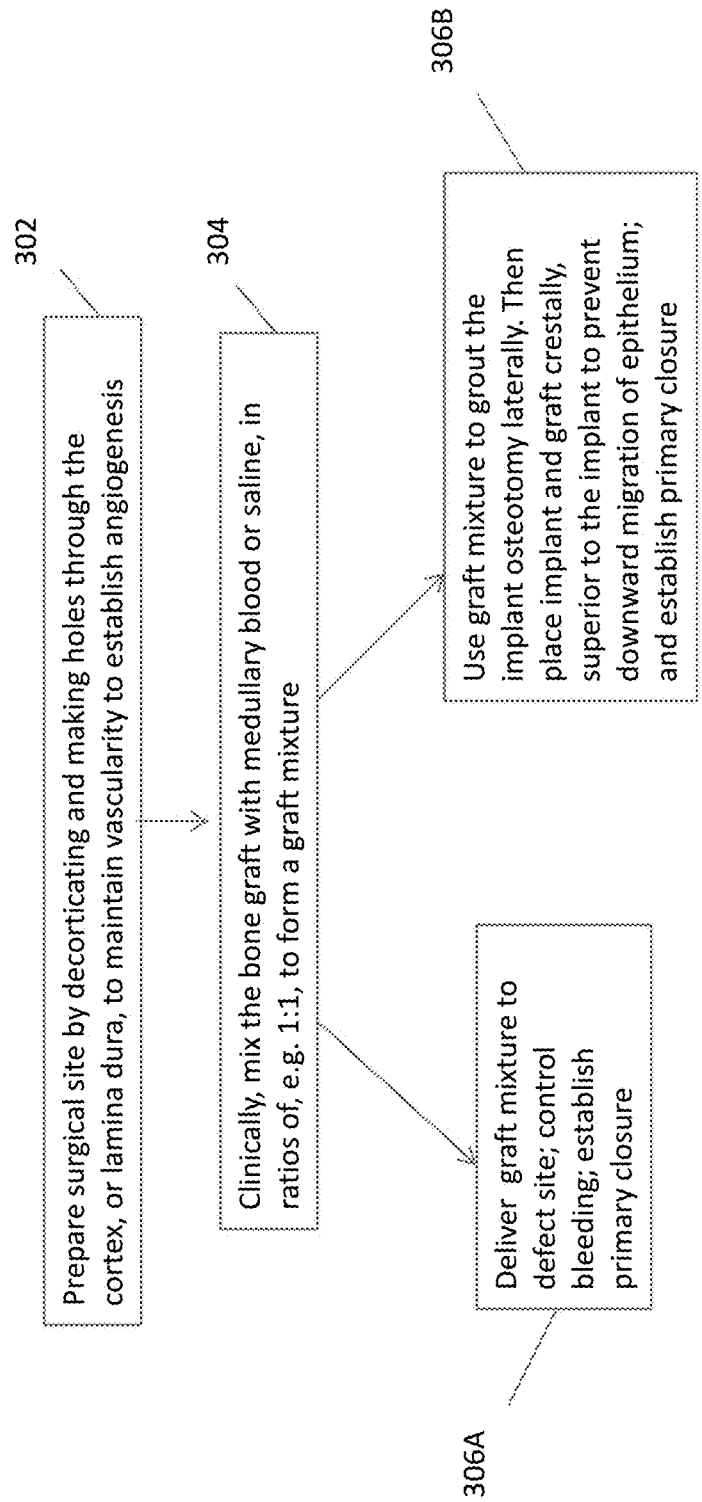

FIG. 13 shows a block diagram of a method for delivering the sterilized crystal composition of FIG. 12.

Figure 14:
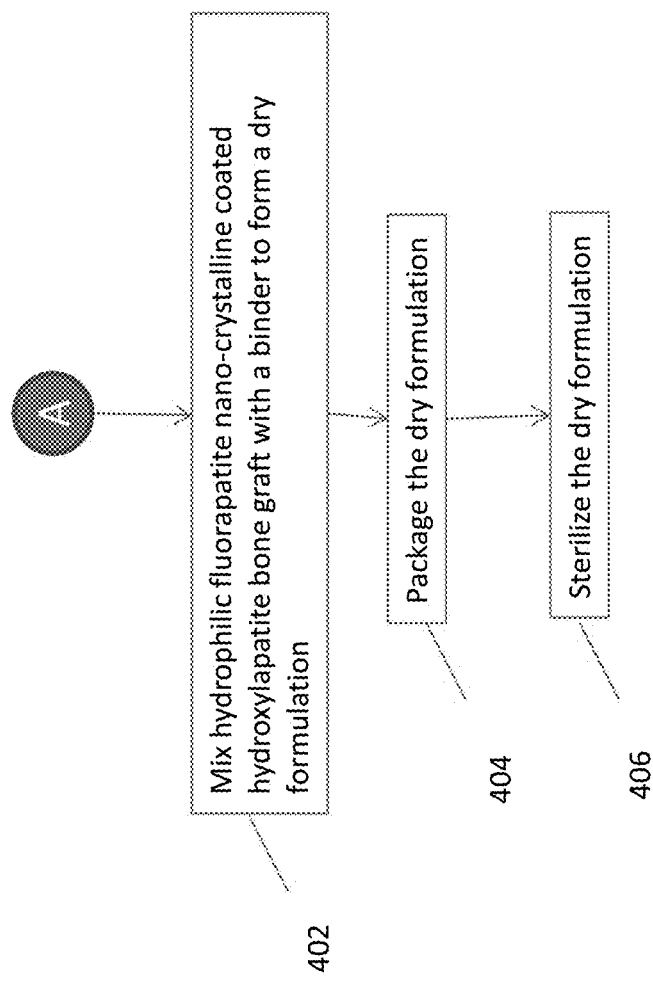

FIG. 14 shows a block diagram of a method for preparing a dry formulation, comprising the novel bone graft, to be used as a component of a putty for end use.

Figure 15:
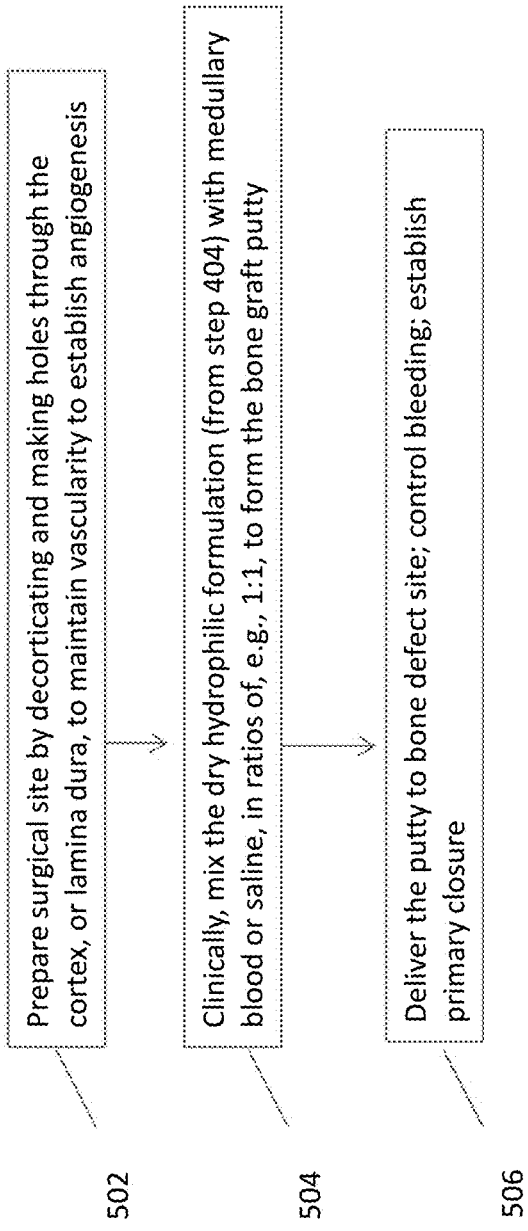

FIG. 15 shows a block diagram of a method for delivering the putty of FIG. 14.

Figure 16:
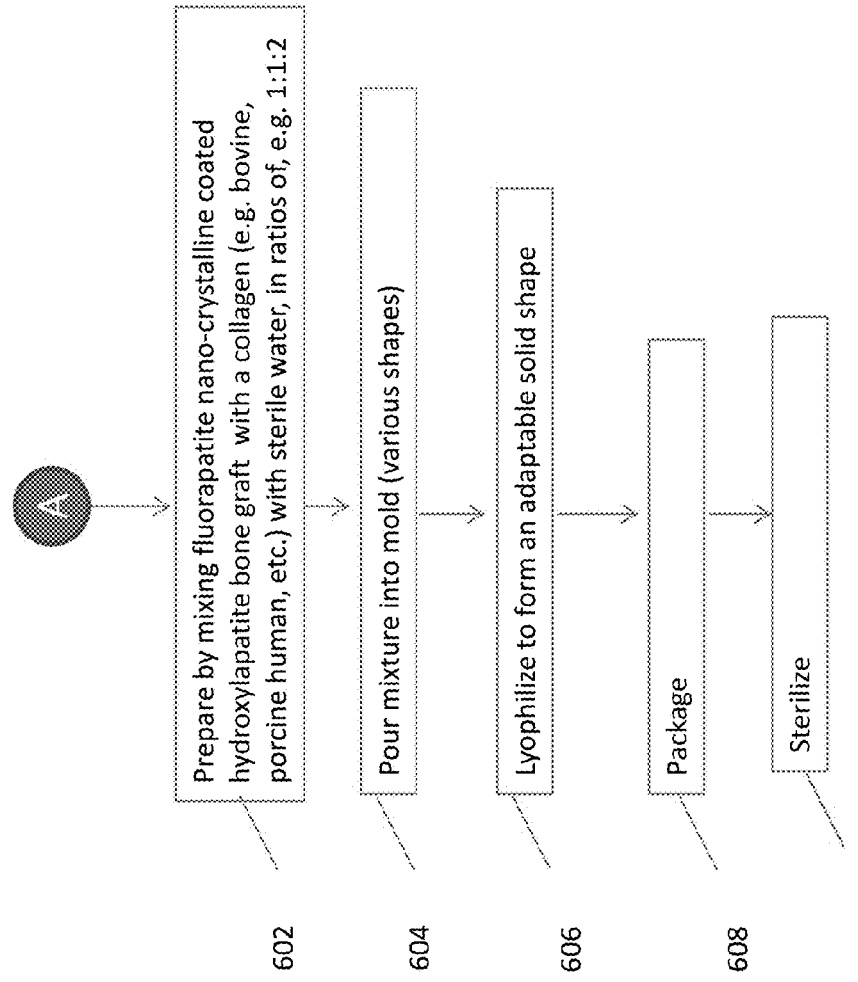

FIG. 16 shows a block diagram of a method for preparing a solid adaptable shape comprising the novel bone graft for end use.

Figure 17:
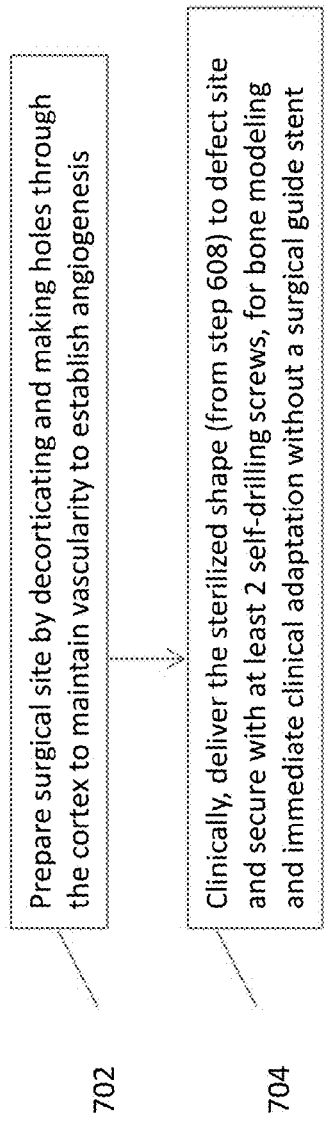

FIG. 17 shows a block diagram of a method for delivering the pre-formed solid adaptable shape of FIG. 16.

Figure 18:
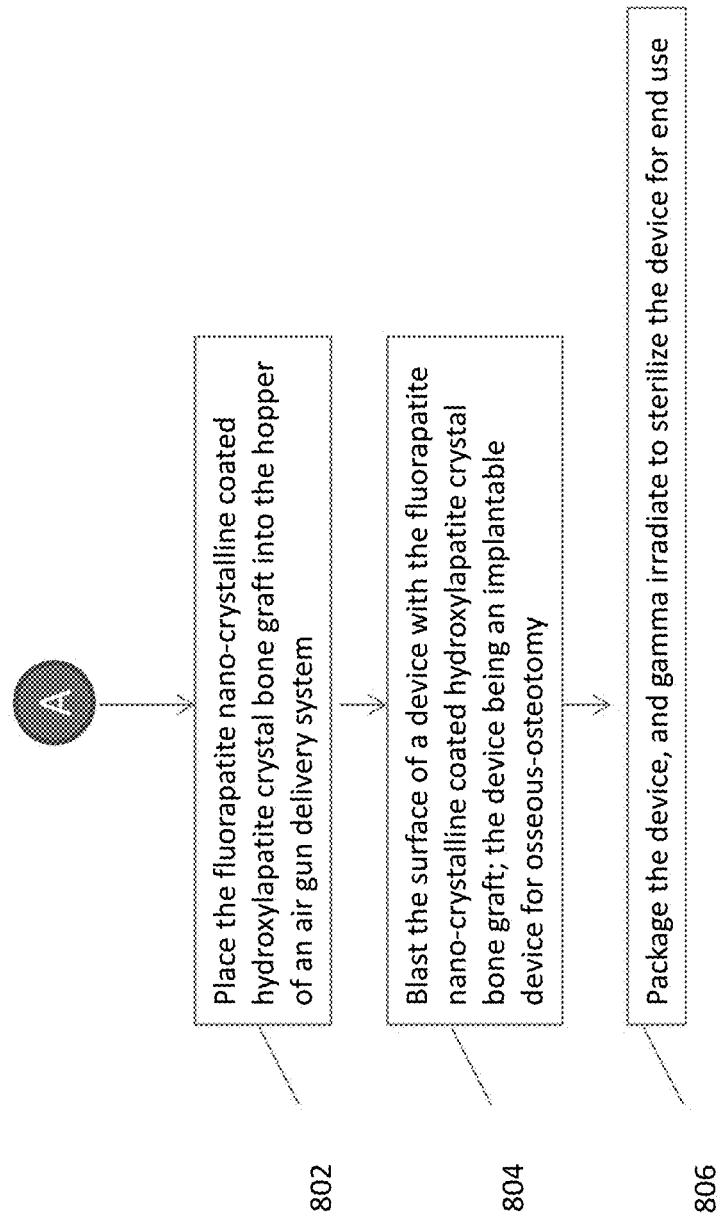

FIG. 18 shows a block diagram of a method for preparing a bioactive interface on a surface of an implantable device, the bioactive interface comprising the novel bone graft, for end use.

Figure 19:
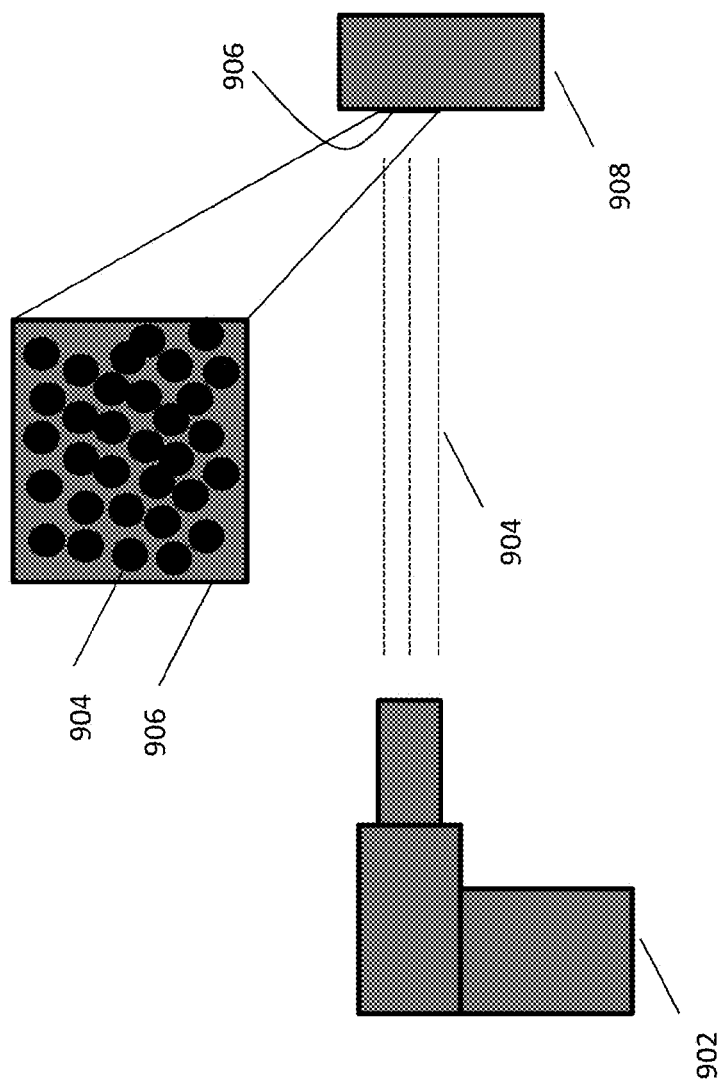

FIG. 19 shows a schematic diagram of a method for preparing a bioactive interface, comprising the novel bone graft, on the surface of an implantable device; and a detail view of the bone graft deposited on a surface of the device (implant).

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DESCRIPTION

Bone graft compositions and methods are provided for inducing cellular development, e.g., bone regeneration, by cell differentiation, proliferation, recruitment, and migration to restore bone at a defect site (e.g., without limitation, dental, periodontal, and orthopedic), and further to promote osteogenesis. Embodiments of the novel bone graft comprise one of: fluorapatite nano-crystalline coated hydroxylapatite crystals; and a combination of fluorapatite nano-crystalline coated hydroxylapatite crystals and fluorapatite nano-crystalline coated hydroxylapatite crystal clusters. The fluorapatite nano-crystalline coated hydroxylapatite crystals comprise a fluorapatite nano-crystalline coating chemically bound to a surface of a surface of non-ceramic hydrophilic hydroxylapatite crystals. The fluorapatite nano-crystalline coated hydroxylapatite crystal clusters comprise a fluorapatite nano-crystalline coating chemically bound to non-ceramic hydrophilic hydroxylapatite crystal clusters. When a plurality of cells are treated with the novel bone graft, for example, through the novel methods provided herein, the bone graft releases fluorapatite to a cellular environment of the plurality of cells in a time-release mechanism.

In other words, the bone graft comprises fluorapatite nano-crystalline coated hydroxylapatite crystals. In some embodiments, the bone graft may further comprise fluorapatite nano-crystalline coated hydroxylapatite crystal clusters. A surface of the fluorapatite nano-crystalline coated hydroxylapatite crystals comprises a fluorapatite nano-crystalline coating. A surface of the fluorapatite nano-crystalline coated hydroxylapatite crystal clusters also comprises the fluorapatite nano-crystalline coating.

Novel methods of the present invention provide treating cells with the novel bone graft, the bone graft comprising a fluorapatite nano-crystalline coating chemically bound to: (a) a surface of hydroxylapatite crystals, or (b) a surface of hydroxylapatite crystals and crystal clusters, wherein the fluorapatite nano-crystalline coating immediately and continuously releases fluorapatite to the cellular environment in a "time release" fashion.

The terms "coat", "coating", and "coated" herein mean chemically bound or fused. The chemical bonds are created by chemical reaction and conversion.

With respect to the term "fluoride," it is intended to encompass the fluoride anion, its conjugate acid, sodium fluoride, fluorapatite preparations, and any mineralized forms including, but not limited to fluorite/fluorspar. For example, methods described herein for treating cells with compositions such as fluorapatite nano-crystalline coated hydroxylapatite crystals and clusters result in the immediate and slow release over time of fluorapatite from the crystal surface to the cellular environment for bone regeneration. As such, the term "fluoride," may individually reference fluoride anion, its conjugate acid, sodium fluoride, fluorapatite preparations, and any mineralized forms, or it may reference any combination of the foregoing.

The "cellular environment" as used herein includes approximately the area directly surrounding the subject cells being treated and approximately the area directly in contact with the subject cells in the extracellular fluid of the bone matrix endostially. Such cellular environment includes, but is not limited to, in vitro, in vivo, ex vivo, and in situ cellular environments. In vitro, in vivo, and ex vivo cellular environments, include, for example, experimental and/or testing environments such as those provided herein. An in situ cellular environment includes, for example, a cellular environment belonging to and part of a living organism (for e.g., osseous development in defective sites).

The novel compositions and methods recruit "bone-building cells" (such as osteoclasts, and osteoblasts) to a defect site over time in order to lay down new bone formation. The inventive chemotactic methods and compositions demonstrate benefits including but not limited to connective tissue control and epithelial cell inhibition. Methods include promoting bone regeneration, by recruitment of osteoprogenitor cells/undifferentiated stem cells to a bone defect site for differentiation, migration, and proliferation as osteoblasts and osteoclasts, etc. Initially, at delivery, cells adjacent to the bone defect site are treated, promoting recruitment of further cells, differentiation, migration, proliferation, and therefore, osteogenesis. The novel compositions and methods control or inhibit in a chemotactic fashion the processes of connective tissue migration and epithelial cell growth to bone defect sites, resulting in better bone restoration by cells, such as osteoblasts and osteoclasts. Moreover, inflammatory cells are inhibited and bacteria are eliminated at the surgical site, further enhancing bone restoration.

Before the invention is described in greater detail, it should be understood by those having ordinary skill in the art that the invention is not limited to the particular embodiments described and/or illustrated herein, as such embodiments may vary. It should also be understood that a particular embodiment described and/or illustrated herein has elements which may be readily separated from the particular embodiment and combined with elements of any of several other embodiments described herein without departing from the scope or spirit of the invention. The headings and captions contained herein are for convenience of reference only and in no way limit the scope or intent of the invention.

It should also be understood by those having ordinary skill in the art that the terminology used herein is for the purpose of describing particular embodiments by formulation of intended application, and the terminology is not intended to be limiting, since the scope of the invention will be limited only by the appended claims. Unless indicated otherwise, ordinal numbers (e.g., first, second, third, etc.) are used to distinguish or identify different elements or steps in a group of elements or steps, and do not supply a serial or numerical limitation on the elements or steps of the invention, or embodiments thereof. For example, "first," "second," and "third" elements or steps need not necessarily appear in that order, and the invention, or embodiments thereof, need not necessarily be limited to three elements or steps. It should also be understood that the singular forms of "a," "an," and "the" may include plural references unless the context clearly dictates otherwise.

Unless defined otherwise, all technical and scientific terms used herein have the same meaning as commonly understood by a person having ordinary skill in the art to which the invention belongs.

The embodiments of the invention will now be described in greater detail.

When synthetic bioactive resorbable non-ceramic hydrophilic hydroxylapatite ($Ca_5(PO_4)_3(OH)$) crystals and crystal clusters were treated with an aqueous sodium fluoride preparation (NaF), a bone graft comprising fluorapatite nano-crystalline coating ($Ca_5(PO_4)_3F$) chemically bound to the surface of the hydroxylapatite crystals and crystal clusters was produced. The novel bone graft maybe used to treat a plurality of cells such as osteoclasts, osteoblasts and epithelial cells.

In vitro studies using osteoblast-like MG-63 human cells treated with the inventive novel bone graft revealed cellular differentiation of such cells. This was further evidenced by osteogenic differentiation by the alkaline phosphatase biochemical marker test. In comparison, upon treating cells in vivo, cellular recruitment and osteoclast/osteoblast cellular proliferation to lay down new bone formation was observed by histologic evaluation. This new bone formation was the result of the immediate and slow release of fluorapatite from the bone graft without causing osteoblast cell death by an abnormal event.

The promotion of MG-63 human cell proliferation and differentiation, as demonstrated in the studies described more particularly herein, indicated that the novel bone graft technology is superb for supplying fluorapatite and promoting cellular development to accelerate new bone formation.

As described in more detail below, in situ applications of the novel bone graft and methods of use include, but are not limited to, augmentation and repair of bone defects and sinus elevations, filling tooth extraction sockets and cyst defect removal (e.g., unicameral cyst defects after enucleation in orthopedics), repair of periodontal bone defects, as well as fortifying an implant osteotomy. The bone graft can be delivered to a defect site as a sterilized crystal composition, a putty, a solid adaptable shape, or a bioactive interface of an implantable device. The bone defect site may be created by, for example, without limitation, periodontitis, implantitis, and/or an osteotomy for implant placement.

Novel Bone Graft Composition and Preparation

Hydroxylapatite Crystals and Crystal Clusters

Figure 1:
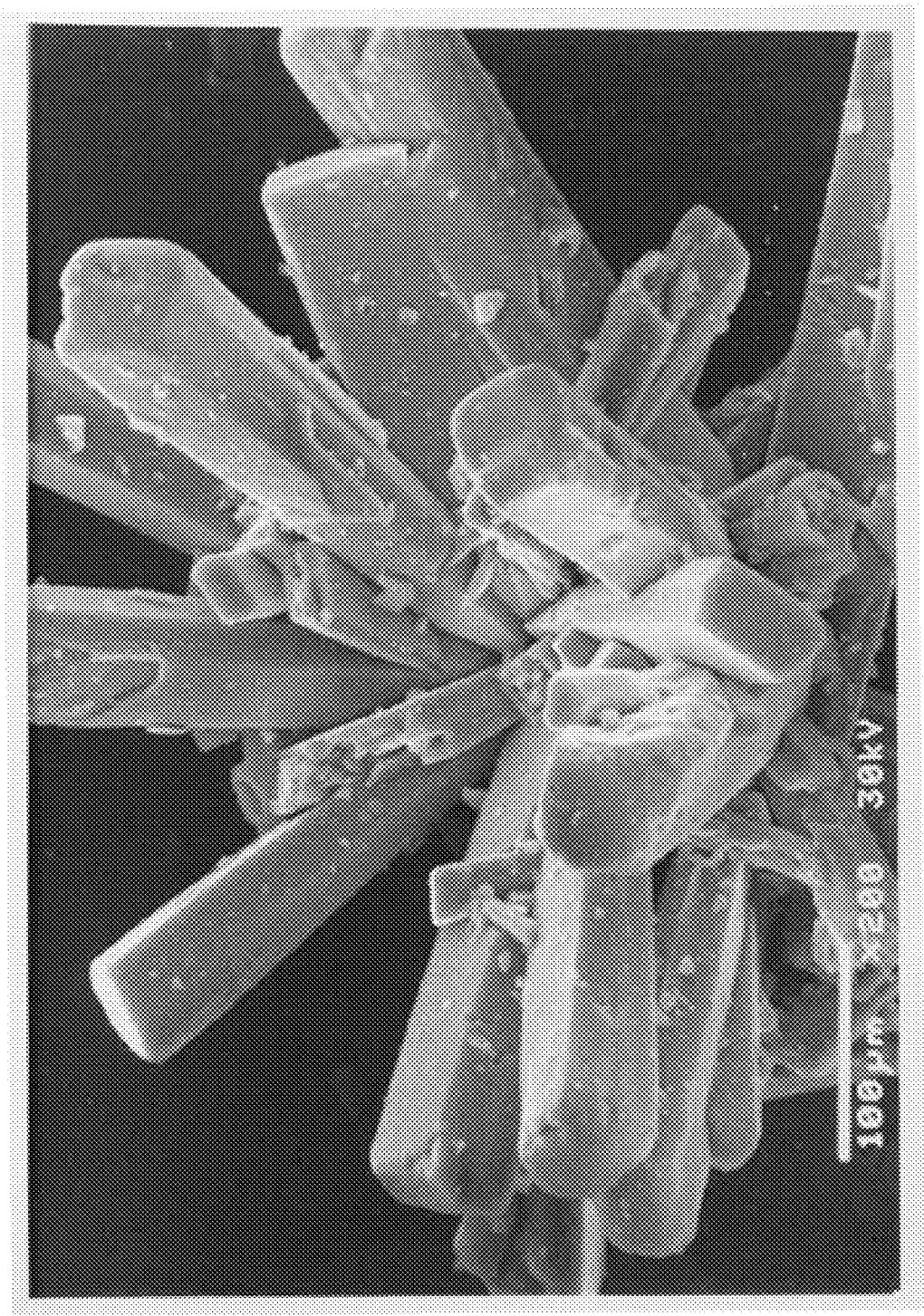

FIG. 1 shows a scanning electron micrograph (SEM) image of a cluster of non-ceramic bioactive resorbable hydroxylapatite crystals (without the fluorapatite nano-crystalline coating). The hydroxylapatite has similar physicochemical properties to human trabecular bone mineral and its crystals in its physicochemical and crystallographic nature. The hydroxylapatite is similar to biological hydroxylapatite crystals, having the same formula: $Ca_5(PO_4)_3(OH)$). Likewise, the hydroxylapatite is bioactive, resorbable, non-ceramic, and hydrophilic. The hydroxylapatite crystals and/or crystal clusters intertwine with one another to provide a three-dimensional trellis, providing a larger surface volume and angular V-shaped mechanical composition (FIG. 1) for hydrophilic absorption of blood or sterile water. The hydroxylapatite crystals/clusters are synthetic, non-ceramic hydroxylapatite having approximately half the amount of impurities as ceramic hydroxyapatite, as determined by the ASTM Committee for ceramics. The fluorapatite nano-crystalline coated hydroxylapatite resulting from the methods of preparation disclosed herein is likewise, bioactive, resorbable, non-ceramic, and hydrophilic.

Physicochemical characterization (e.g., infrared spectroscopy and X-ray diffraction) of ceramic hydroxyapatite granules has shown that it is not like the hydroxylapatite crystals of the novel bone graft. As defined by the International Center for Diffraction Data, one significant difference between the non-ceramic hydroxylapatite crystals ($Ca_5(PO_4)_3(OH)$) of the novel bone graft and ceramic hydroxyapatite granules ($Ca_{10}(PO_4)_6(OH)_2$), including bovine ceramic granules, is that ceramic hydroxyapatite will dehydroxylate under high heat, process known as sintering. When mammalian bone or any synthetic, ceramic hydroxyapatite is heated at high temperatures, they will dehydroxylate and convert to oxyapatite ($Ca_{10}(PO_4)_6O_2$), losing its calcium carbonate groups as well as the hydroxyl groups (OH), the major mineral component of human bone. The significance of this is discussed below. Ceramic hydroxyapatite will further convert to minor phases like tricalcium phosphate (TCP), $Ca_3(PO_4)_2$ and tetracalcium phosphate $Ca_4(PO_4)_2O$. Ceramics have secondary phases of α/β TCP, which makes them biphasic, as well as pyrophosphates acting as bone inhibitors.

In preparing the inventive fluorapatite nano-crystalline coating of the novel bone graft described herein, fluoride displaces the hydroxyl groups of the non-ceramic hydroxylapatite crystal/cluster, to form the nano-crystalline surface coating of fluorapatite ($Ca_5(PO_4)_3F$). Due to the high-temperature sintering process by which ceramic hydroxyapatite granules are prepared, ceramic hydroxyapatites lack the hydroxyl groups (OH) making fluoride displacement of hydroxyl groups impossible in ceramic hydroxyapatite particles. As such, it is not possible to prepare fluorapatite as described herein starting from a ceramic hydroxyapatite $Ca_{10}(PO_4)_6O_2$ lacking the hydroxyl groups.

Non-ceramic hydroxylapatite crystals and crystal clusters include the presence of brushite—$CaHPO_4.2H_2O$, also known as dicalcium phosphate dihydrate (DCPD), and monetite—$CaHPO_4$, also known as dicalcium phosphate (DCP). Neither of which are found in ceramic hydroxyapatite granules because they have been destroyed by high heat. The important relationship between brushite and monetite is controlled during manufacturing of the hexagonal-shaped crystals using a time-related, physicochemical resorption requirement for larger crystal growth and maturation of the three dimensional clusters. Brushite is a prerequisite mineral component for initiation of bone formation, and will slowly resorb and convert to biologic hydroxylapatite in situ. The physical properties of the hexagonal-shaped crystals and 3-dimensional clusters provide a trellis that facilitates cell bone bridging at the defect site. Brushite is chemotactically used to control host collagen (connective tissue) migration at the defect site by its higher chemotactic solubility. Studies have demonstrated that the non-ceramic hydroxylapatite crystal restrains and controls migration of connective tissue at the defect site and will bridge bone across a critical site defect of 8 mm in a 1 mm wide channel. The configuration of the non-ceramic hydroxylapatite crystals and clusters provides more space between the crystals when compared to ceramic hydroxyapatite granules. These spaces facilitate cellular and tissue proliferation into the grafted material in situ, thus enhancing osseointegration and bone formation with progressive crystal resorption.

Sizing of the Hydroxylapatite Crystals and Crystal Clusters

The resorption rate of non-ceramic hydroxylapatite crystals/crystal clusters is regulated by the size of such crystals/crystal clusters. Fluorapatite nano-crystalline coated hydroxylapatite of the present invention is prepared from resorbable non-ceramic hydrophilic hydroxylapatite crystals that are at least 0.01 μm in a shortest dimension and larger crystals and crystal clusters no more than 841 μm in a longest dimension.

In some embodiments, for example, the hydroxylapatite crystals/clusters of the novel bone graft are at least 0.01 μm, 10 μm, 50 μm, 100 μm, 200 μm, 300 μm, 400 μm, 500 μm, 600 μm, 700 μm, or 841 μm in the longest dimension. For example, the hydroxylapatite crystals/clusters are at least 300 μm in the longest dimension. In some embodiments, the hydroxylapatite crystals/clusters are no more than 841 μm, 700 μm, 600 μm, 500 μm, 400 μm, 300 μm, 200 μm, 100 μm, 50 µm, 10 µm, or 0.01 µm in the longest dimension. For example, the hydroxylapatite crystals/clusters are no more than 400 µm in the longest dimension. The hydroxylapatite crystals suitable for preparing fluorapatite nano-crystalline surface technology may also be described using a combination of the foregoing. For example, in some embodiments, the hydroxylapatite crystals/clusters are at least 0.01 µm and no more than 841 µm in the longest dimension, such as at least 200 µm and no more than 500 µm in the longest dimension, and including at least 300 µm and no more than 400 µm in the longest dimension.

Size of the hydroxylapatite used to prepare the novel bone graft varies depending on the intended end use, or desired clinical application, for the bone graft. FIG. 10 shows an approximation of resorption rates of various sizes of the hydroxylapatite crystals and crystal clusters. The desired resorption rate will play a role in the hydroxylapatite chosen for the embodiment of the novel bone graft when treating cells. In some embodiments, the hydroxylapatite crystals of the fluorapatite nano-crystalline coated hydroxylapatite crystals are selected from a size range of 0.001-100 µm. In such embodiments, the bone defect site is a periodontal defect site of an approximate size chosen from the range of 2.5 mm to 5 mm in depth. In other embodiments, the hydroxylapatite crystals and the hydroxylapatite crystal clusters are selected from a size range of 100-500 µm for large periodontal defects. In such embodiments, the bone defect site is typically caused by periodontitis or implantitis the bone defect site is a periodontal defect site of an approximate size of approximately 5 mm by 6 mm in depth. In still other embodiments, the hydroxylapatite crystals and hydroxylapatite crystal clusters are selected from a size range of 150-841 µm. In such embodiments, the bone defect site is at least one of: a dental sinus elevation, or an orthopedic bone defect site comprising a unicameral cyst.

In embodiments, the sizes of the non-ceramic hydroxylapatite crystals/clusters (reacted with NaF to form the inventive fluorapatite nano-crystalline coating on the hydroxylapatite) are of a uniform or homogeneous size. In an exemplary embodiment, the crystals are substantially all small. In other embodiments, the sizes of the non-ceramic hydroxylapatite crystals/clusters are of a non-homogeneous size, i.e., a combination of small and large. For example, a size in the range of approximately 00-100 µm is referred to herein as "small", and a size in the range of approximately 101 to 841 µm is referred to herein as "large". While crystals may be small or large, clusters are typically large. In some embodiments, the ratio of small crystals to large crystals and crystal clusters is 50/50, 55/45, 60/40, 65/35, 70/30, 75/25, 80/20, 85/15, 90/10, 95/05. In an exemplary embodiment, the majority of the crystals (e.g., approximately 70%), are small, i.e., in the range of 37 µm to 100 µm, with the largest crystals/clusters (30%), being as high as 841 µm.

It will be recognized that these disclosed sizes and combinations thereof are exemplary and are no way meant to limit the invention. It should further be recognized that the resulting fluorapatite nano-crystalline coated hydroxylapatite may be the substantially the same size as the reacted hydroxylapatite, so size of hydroxylapatite and size of fluorapatite coated hydroxylapatite may be discussed herein interchangeably.

Method of Preparing the Novel Bone Graft

As shown in FIG. 11, in some embodiments of the present invention, the method for preparing a fluorapatite nano-crystalline coated hydroxylapatite bone graft comprises the following steps. Sieving at least one of non-ceramic hydrophilic hydroxylapatite crystals, and non-ceramic hydrophilic hydroxylapatite crystal clusters, to achieve a desired size or size range (step 102). Blending the sieved at least one of non-ceramic hydrophilic hydroxylapatite crystals and non-ceramic hydrophilic hydroxylapatite crystal clusters (step 103). Immerse the blended at least one of non-ceramic hydrophilic hydroxylapatite crystals and non-ceramic hydrophilic hydroxylapatite crystal clusters in a solution comprising sodium fluoride (e.g., 4% NaF) to form a fluorapatite nano-crystalline coated hydroxylapatite bone graft (step 104).

The initial concentration of hydroxylapatite immersed in the solution of sodium fluoride may be at least 1 g and no more than 12 g hydroxylapatite per 60 mL of the sodium fluoride solution. In some embodiments, the initial concentration of hydroxylapatite in the solution of sodium fluoride is at least 1 g, 2 g, 3 g, 4 g, 5 g, 6 g, 7 g, 8 g, 9 g, 10 g, 11 g, or 12 g hydroxylapatite crystals per 60 mL of the sodium fluoride solution. For example, the initial concentration of hydroxylapatite in the solution of sodium fluoride is at least 5 g hydroxylapatite per 60 mL of the sodium fluoride solution. In some embodiments, the initial concentration of hydroxylapatite in the solution of sodium fluoride is no more than 12 g, 11 g, 10 g, 9 g, 8 g, 7 g, 6 g, 5 g, 4 g, 3 g, 2 g, or 1 g hydroxylapatite per 60 mL of the sodium fluoride solution. For example, the initial concentration of hydroxylapatite in the solution of sodium fluoride is no more than 7 g hydroxylapatite per 60 mL of the sodium fluoride solution. The initial concentration of hydroxylapatite in the solution of sodium fluoride may also be described using a combination of the foregoing. For example, in some embodiments, the initial concentration of hydroxylapatite in the solution of sodium fluoride is at least 1 g and no more than 12 g hydroxylapatite per 60 mL of the sodium fluoride solution, such as at least 5 g and no more than 7 g hydroxylapatite crystals per 60 mL of the sodium fluoride solution, and including at least 6 g hydroxylapatite per 60 mL of the sodium fluoride solution or no more than 6 g hydroxylapatite per 60 mL of the sodium fluoride solution.

A typical reaction time for the reaction between hydroxylapatite and sodium fluoride is selected from the range of approximately 2-3 minutes, but in some embodiments, may be at least 0.1 minutes and no more than 6 minutes. In some embodiments, the reaction time for the reaction between hydroxylapatite crystals and sodium fluoride may be at least 0.1, 0.5, 1.0, 1.5, 2.0, 2.5, 3.0, 3.5, 4.0, 4.5, 5.0, 5.5, 6.0 minutes. For example, the reaction time for the reaction between hydroxylapatite and sodium fluoride is at least 1.0 minute. In some embodiments, the reaction time for the reaction between hydroxylapatite crystals and sodium fluoride may be no more than 6.0, 5.5, 5.0, 4.5, 4.0, 3.5, 3.0, 2.5, 2.0, 1.5, 1.0, 0.5, or 0.1 minutes.

Following the immersion step 104, remove the fluorapatite nano-crystalline coated hydroxylapatite bone graft from the solution (step 106). Next, wash the fluorapatite nano-crystalline coated hydroxylapatite bone graft with, e.g., saline, deionized water (step 108). It will be recognized that other solutions/liquids may be used to wash the bone graft, and the invention includes all such feasible solutions/liquids. In some embodiments, the method further comprises testing the bone graft for free fluoride (step 107) after the washing step, and repeating the washing step until it is determined that a desired amount of free fluoride is detected for a specific osseous defect or clinical application. The washing step may repeated until a negligible amount of free fluoride is detected, the negligible amount being determined in reference to end use requirements. After the washing 108 and/or testing 107 steps, dry the fluorapatite nano-crystalline coated hydroxylapatite bone graft (step 110).

The washed fluorapatite nano-crystalline crystal/cluster surfaces were subjected to analyses using scanning electron microscopy (SEM), one- and two-dimensional X-ray diffraction, energy dispersive X-ray (EDX) analysis, and EDX mapping. The reaction of fluoride ions with the non-ceramic hydroxylapatite possessing the hydroxyl group (OH) produced a nano-crystalline fluorapatite surface technology having characteristic and sharp X-ray diffraction patterns on the surface of the underlying crystals/clusters. EDX analysis revealed a fluorapatite peak at 0.70 KeV that was not seen on the surface of non-fluoridated control crystals/clusters. Furthermore, EDX mapping showed an evenly distributed needle crystalline particulate pattern that adhered to the underlying crystal surface by chemical conversion to form the fluorapatite nano-crystalline coating. It was concluded that the reaction of synthetic, non-ceramic resorbable hydroxylapatite with 4% sodium fluoride produced a fluorapatite nano-crystalline coating on the hydroxylapatite surface, comprising loosely and firmly bound fluorapatite crystallites. This suggests that fluorapatite nano-crystalline surface technology can act as a source of controlled fluorapatite release and, therefore, when it is used as a bone graft biomaterial, demonstrates excellent stimulation for bone growth (FIGS. 7 and 8).

Compositions Comprising the Novel Bone Graft and Delivery Methods Thereof

The bone graft is delivered to the bone defect site for treatment of a plurality of cells. Cells adjacent to the bone defect site are initially treated, followed by recruitment, differentiation, proliferation, migration, etc. of further cells into the bone defect site. The novel bone graft may be delivered to the defect site as a sterilized crystal composition, putty composition, adaptable solid (pre-formed shape) composition, or bioactive implant interface. The further steps in preparation are based on whether the non-ceramic fluorapatite nano-crystalline coated hydroxylapatite bone graft is to be delivered to the defect/surgical site for treatment of the plurality of cells as a sterilized crystal composition, putty, pre-formed adaptable shape, or bioactive implant interface. It should be noted that the non-ceramic fluorapatite nano-crystalline coated hydroxylapatite bone graft, and the resulting sterilized crystal composition, putty (and associated dry formulation), and pre-formed adaptable shape are hydrophilic.

Sterilized Crystal Composition

As shown in FIG. 12, in some embodiments, the novel bone graft is delivered to the cells as a sterilized crystal composition. To prepare the sterilized crystal composition, following step 110 (FIG. 11), the bone graft is packaged (step 202) and sterilized for end use (step 204).

FIG. 13 shows an exemplary method of delivering of the sterilized crystal composition. The surgical site is prepared by decorticating and making holes through the cortex, or lamina dura, to maintain vascularity and establish angiogenesis (step 302). The sterilized crystal composition is mixed with medullary blood or saline in ratios of e.g. 1:1 (step 304). Next, the sterilized crystal composition is delivered to the defect site, followed by controlling bleeding and establishing primary closure (step 306A); or alternatively, delivered by grouting an implant osteotomy with the mixture laterally, followed by placing the implant and grafting crestally (superior to the implant to prevent downward migration of epithelium) then establishing primary closure (step 306B).

Putty

As shown in FIG. 14, in some embodiments, the novel bone graft is delivered as a putty. To prepare the putty, a dry formulation is prepared, followed by clinical mixing during delivery. To prepare the dry formulation, following step 110 (FIG. 11), the fluorapatite nano-crystalline coated hydroxylapatite crystal composition is mixed with a binder to create a dry formulation (step 402). The method of claim 3B, wherein a ratio of the bone graft to the binder is between 9:1 and 8:2. Examples of binders comprise: binder is selected from the group comprising: Synthetic Povidone K90 BASF (preferably); a combination of Poloxamer 407 and water; a combination of lecithin and water; a combination of glycerol and water; a combination of human collagen and water; a combination of porcine gelatin and water; a combination of calcium sulfate, carboxymethyl-cellulose, and water; or a combination of hyaluronic acid and water. It will be recognized that these binders are provided for the purpose of disclosure, and not meant to limit the invention. The scope of the invention includes any suitable binder. Following mixing (step 402), the dry formulation is packaged (step 404), and then sterilized (step 406).

FIG. 15 shows an embodiment of a method for delivering the bone graft as a putty. The surgical site is prepared by decorticating and making holes through the cortex, or lamina dura, to maintain vascularity and establish angiogenesis (step 502). The dry crystal formulation (prepared in FIG. 14) is mixed with medullary blood or saline in a ratio of, e.g., 1:1, to create the putty (step 504). The putty is then delivered to the bone defect/surgical site; followed by controlling bleeding and establishing primary closure (step 506).

Pre-Formed Adaptable Solid Shape

As shown in FIG. 16, in some embodiments, the novel bone graft is delivered as an adaptable pre-formed solid shape. In such embodiments, to prepare the adaptable solid shape, followed by drying step 110 (of FIG. 11), the bone graft is mixed with collagen (i.e. bovine, porcine, human etc.) and sterile water (e.g., without limitation, in a ratio of, 1:1:2), to create a mixture (step 602). Next, the mixture is poured into a mold of the desired shape (step 604). The shaped mixture is then lyophilized (step 606) to form a solid adaptable shape, in the shape of the mold. The solid adaptable shape is packaged (608), and then sterilized (step 610), for end use.

FIG. 17 shows a method for delivery of the pre-formed solid adaptable shape. The surgical site is prepared by decorticating and making holes through the cortex, to maintain vascularity and establish angiogenesis (step 702). The pre-formed solid adaptable shape is then delivered to the bone defect and/or surgical site and secured, for example, without limitation, with two self-drilling screws (step 704), for bone modeling and immediate clinical adaptability, without a surgical guide stent.

Bioactive Implant Interface

As shown in FIGS. 18 and 19, in some embodiments, the bone graft may be used to create a physiologic surface deposition on a surface of a device, the device being implantable into a bone defect site. The implantable device may comprise, for example, at least one of titanium or plastic. The implantable device may be for dental, periodontal, or orthopedic applications (e.g., without limitation, tooth implants, hip replacements, spinal implant augmentation, etc.). The surface deposition enables immediate cell activation by such surface to adapt to bone in a faster biologic fashion than the conventional time period of fibro-osseointegration. Therefore, the surface is not only for cleaning and passivation, but also to develop a biologic surface interface for rapid biointegrative activity, to speed production of the cells by 2-fold to achieve faster bone adaptation.

As shown in FIG. 18, to develop the bioactive implant interface, following step 110, the bone graft is lodged into the surface of the implantable device. The lodging may be accomplished through, for example, the hopper of an air gun (902) (e.g. Scales Industrial Technologies, Carle Place, N.Y.) being loaded with the crystal composition (step 802), which is used to blast the fluorapatite nano-crystalline coated hydroxylapatite crystal composition (904) (produced by the methods described herein above) at a surface (906) of the device (908) (step 804). The blasting may be between approximately 50 psi to 200 psi air pressure, depending on the system used or desired application. For example, in some embodiments, the pressure may be 50 psi. In other embodiments, the pressure may be 100 psi. In still yet other embodiments, the pressure may be 150 psi. In yet other embodiments, the pressure may be 200 psi. In some embodiments, the pressure may be a continuous pressure, and in some embodiments, the pressure may be variable. These examples are not meant to be limiting, and the scope of the invention includes any suitable air pressure between approximately 50 psi and 200 psi. Since titanium elastic modulus is 15 million, much lower than stainless steel, the blasted fluorapatite nano-crystalline coated hydroxylapatite gets lodged to the titanium surface. The device comprising of the bioactive implant interface, is then packaged and sterilized for end use (step 806).

FIG. 19 shows a detail view of the air blasting system used to prepare the implant interface, wherein fluorapatite nano-crystalline coated hydroxylapatite (904) lodged on a surface (906) of the device (implant) (908). Thereafter, the implant gets appropriately packaged and ready for gamma sterilization. The implant surface morphology is improved, having a bioactive mineralized fluorapatite nano-crystalline coated hydroxylapatite crystal coating thereon, for quicker bone cell adaptation to the titanium interface for faster bone adaptation. The disadvantage of prior art technology related to having implant cleaning by glass bead products, aluminum oxide medium or sand blasting is that all such materials had to be removed by very complicated acid formulation, and are only used to create a roughened titanium interface, not a bioactive interface. According to all such blasting materials, some remained embedded on the surface of titanium interface incorporated with a mixture of acid formulation followed by bone breakdown and implant failure.

In embodiments of the invention, packaging may comprise placing in a bottle, vial, bag, box, etc. or any other suitable containers. Sterilization may be achieved via gamma radiation, however, any method of sterilizing, now known or hereafter developed, is included within the scope of the invention.

Time Release Mechanism and Accelerated Rate of Crystal Resorption

While experimentally, immediate release to the cellular environment of fluorapatite from the inventive fluorapatite nano-crystalline surface technology was observed, the concentration of fluorapatite in the cellular environment continued to increase gradually over time as a "time-release mechanism". In some embodiments, small crystals provide an immediate release of fluorapatite as a "first stage" of crystal dissolution approximately delineated by 0-4 hours after treatment (for a biologic cell reaction and immediate recruitment of osteoclast followed by osteoblast cells, within the cellular environment), followed by release from large crystals/clusters in a "second stage" approximately delineated by 8-48 hours after treatment. As discussed above, the larger underlying hydroxylapatite crystals and crystal clusters provide a trellis-like formation for cell reaction and recruitment, and bone bridging across the entire defect site to complete bone restoration. The inventive composition and method results in substantially-continuous bone mineralization of the defect site as the fluorapatite is released in a controlled, i.e., time release, manner.

Referring to FIG. 9, there is shown a Scanning Electron Micrograph of the large hydroxylapatite crystal surface comprising fluorapatite nano-crystalline surface technology. Fluorapatite crystallites of the fluorapatite nano-crystalline coating may be either "firmly" bound or "loosely" bound to the hydroxylapatite crystal. As used herein, "firmly" bound refers to fluorapititee crystallites that are bound directly to coat the entire surface of the hydroxylapitite crystals and crystal clusters, and "loosely" bound refers to fluorapatite crystallites that are bound, yet not directly, i.e., scattered, on the hydroxylapitite surface and on top of the other fluorapatite crystallites in the nano-crystalline coating. The entire surface is covered with an evenly distributed refined nano-crystalline coating of firmly bound fluorapatite crystallites due to direct chemical conversion on the surface. These are considered firmly bound fluorapatite nano-crystalline because they are approximately and directly bound to the crystal surface of the underlying non-ceramic hydroxylapatite crystal (see the rectangle and square areas). There are several areas of elevated chunks of fluorapatite of nano-crystalline coating, which are loosely bound fluorapatite crystallites. This is because they are fighting for "real estate" on the surface of the hydroxylapatite crystal, so they attach (or lay) themselves on top of the firmly bound fluorapatite nano-crystalline, but are not directly bound to the surface of the hydroxylapatite crystal, as noted by the areas referenced by the triangles. Typically, loosely bound fluorapatite crystallites of the nano-crystalline coating are first released to the cellular environment, followed by firmly bound fluorapatite crystallites of nano-crystalline coating due to, differences in solubility of firmly and loosely bound fluorapatite crystallites. Once the nano-crystalline surface has released most of the loosely and firmly bound fluorapatite crystallites to the cellular environment, additional fluorapatite is released from spaces between the hydroxylapatite crystal lattice, also in a time-released fashion as the crystals/clusters degrade and resorb.

The time-release mechanism of the present invention is slowly depleted over an extended time period, which varies depending on the patient's age or metabolism, and size of the underlying crystal. This controlled method of fluorapatite time-released dissolution increases resistance against acid destruction of bone to prevent bone breakdown and caries, allowing successful bone restoration of the defect site at an accelerated rate twice as fast as the normal rate. Previous fluorapatite formulations, compositions and methods showed bone formation concurrent to "rate of resorption", at best, in 20-21 weeks on average depending on patient's metabolism or age without a jumpstart crystal formulation. On average, though, with the present inventive fluorapatite composition and method produce new bone formation in 6-8 weeks in a younger person, and 7 to 11 weeks in an older person. FIG. 10 shows fluorapatite nano-crystalline coated hydroxylapatite crystal size vs. resorption rate by histologic evaluation and bone formation in rabbits compared to humans.

Evidence of the accelerated rate of resorption was observed by histologic evaluation in a rabbit defect after 4 weeks (FIGS. 7 and 8). FIG. 7 provides animal histology in vivo, showing an advancing ossification front of osteoblast cells due to fluorapatite nano-crystalline resorption and bone build up, for lamellar bone formation, with osteoblast cells in their lacunae designating faster bone maturation. Note a large hydroxylapatite crystal lower left designated for bone bridging. FIG. 8 provides animal histology in vivo, showing hydroxylapatite, comprising the inventive surface technology, while in their last phase of resorption; noting an osteocyte within the fluorapatite crystal, which is surrounded by bone while undergoing a metamorphic conversion to mature bone formation, noted by the yellow oval.

Fluorapatite Released from the Novel Bone Graft

Fluorapatite Concentration

Figure 2:
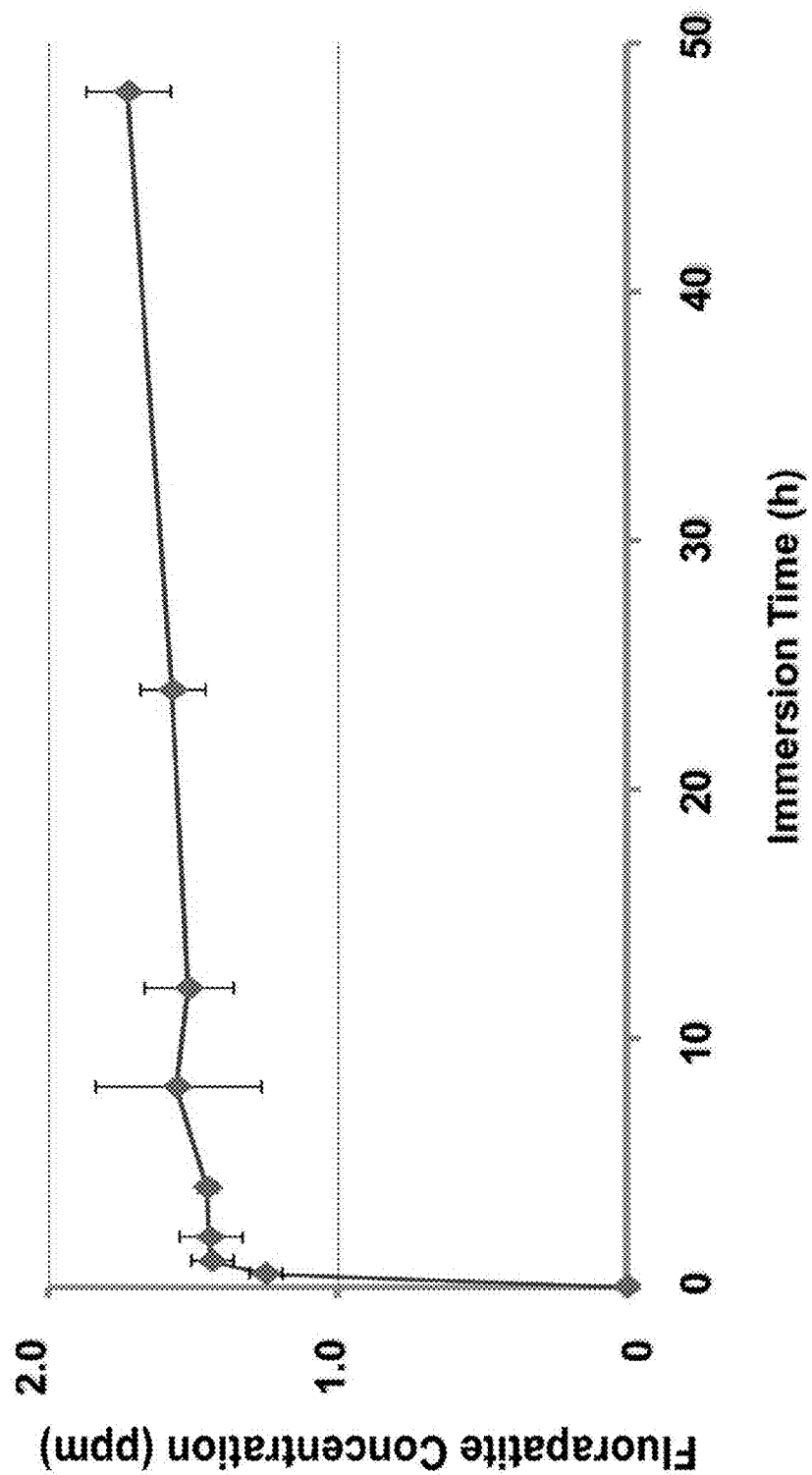

FIG. 2 provides the concentration of fluorapatite released into culture medium over time. Table 1 herein below shows the same information in table form. The fluorapatite was released into culture medium from fluorapatite nano-crystalline surface technology of the present invention. Release of fluorapatite was measured with a fluoride ion-selective electrode as described in Materials and Methods herein below. Filled diamonds (and the bars there between) represent mean values with standard error (vertical bars). The concentration of fluorapatite released from the fluorapatite nano-crystalline coating was increased markedly (1.25±0.05 ppm) at 30 minutes after immersion of the fluorapatite nano-crystalline coated hydroxylapatite. The concentration gradually increased (1.57±0.12 ppm) at 24 hours, and peaked at 48 hours (1.73±0.15 ppm), thus confirming the immediate release as first phase and the slow release as second phase (see Table 1 below) from the fluorapatite nano-crystalline coated surface of the hydroxylapatite crystals and clusters.

TABLE 1

| Hours | % of Fluorapatite Release (average) | Type of Fluorapatite Bound to the Crystal Surface | Summary of Released Fluorapatite | Phase |
|---|---|---|---|---|
| 0.5 | 60.00% | Loosely Bound | Averages of 65-67% FA released within first 4 hours | First Stage |
| 1 | 65.00% | Loosely Bound | | |
| 2 | 70.00% | Loosely Bound | | |
| 4 | 70.00% | Loosely Bound | | |
| 8 | 75.00% | Firmly Bound | Average of 75% FA released within 8-48 hours | Second Stage |
| 12 | 70.00% | Firmly Bound | | |
| 24 | 75.00% | Firmly Bound | | |
| 48 | 80.00% | Firmly Bound | | |

Experiments showed that the fluorapatite nano-crystalline surface technology has an antibacterial effect, which, in the context of regenerating new bone formation, appears to be a first step in a stepwise process: 1) antibacterial effects are expressed (by, e.g., preventing caries) near the site of treatment, where fluorapatite concentrations are highest, and 2) fluorapatite is slowly released from the fluorapatite nano-crystalline coating to facilitate osteogenesis at a defect site, for example, a wound site with or without primary closure. In vitro experiments showed that at least 20% and no more than 60% of the fluorapatite released by fluorapatite nano-crystalline coating in a period of 24-hours was released within the first 30 minutes of immersion. In some embodiments, for example, at least 20%, 25%, 30%, 35%, 40%, 45%, 50%, 55%, or 60% of the fluorapatite released to the cellular environment is released within the first 30 minutes. For example, at least 20% of the fluorapatite released to the cellular environment is released within the first 30 minutes. In some embodiments, no more than 60%, 55%, 50%, 45%, 40%, 35%, 30%, 25%, or 20% of the fluorapatite released to the cellular environment is released within the first 30 minutes. For example, no more than 60% of the fluorapatite released to the cellular environment is released within the first 30 minutes. The percentage of fluorapatite released to the cellular environment within the first 30 minutes may also be described using a combination of the foregoing. For example, in some embodiments, at least 30% and no more than 60% of the fluorapatite released to the cellular environment is released within the first 30 minutes, such as at least 40% and no more than 60% of the fluorapatite released to the cellular environment is released within the first 30 minutes, including at least 50% and no more than 60% of the fluorapatite released to the cellular environment is released within the first 30 minutes. In another non-limiting example, at least 60% of the fluorapatite released to the cellular environment is released within the first 30 minutes. In yet another non-limiting example, no more than 60% of the fluorapatite released to the cellular environment is released within the first 30 minutes.

It is also useful to describe the percentage of fluorapatite released to the cellular environment within the first 60 minutes. In vitro experiments further showed that at least 25% and no more than 65% of the fluorapatite released by fluorapatite nano-crystalline coating in a period of 24-hours was released within the first 60 minutes. In some embodiments, at least 25%, 30%, 35%, 40%, 45%, 50%, 55%, 60%, or 65% of the fluorapatite released to the cellular environment is released within the first 60 minutes. For example, at least 25% of the fluorapatite released to the cellular environment is released within the first 60 minutes. In some embodiments, no more than 65%, 60%, 55%, 50%, 45%, 40%, 35%, 30%, or 25% of the fluorapatite released to the cellular environment is released within the first 60 minutes. For example, no more than 65% of the fluorapatite released to the cellular environment is released within the first 60 minutes. The percentage of fluorapatite released to the cellular environment within the first 60 minutes may also be described using a combination of the foregoing. For example, in some embodiments, at least 35% and no more than 65% of the fluorapatite released to the cellular environment is released within the first 60 minutes, such as at least 45% and no more than 65% of the fluorapatite released to the cellular environment is released within the first 60 minutes, including at least 55% and no more than 65% of the fluorapatite released to the cellular environment is released within the first 60 minutes. In another non-limiting example, at least 65% of the fluorapatite released to the cellular environment is released within the first 60 minutes. In yet another non-limiting example, no more than 65% of the fluorapatite released to the cellular environment is released within the first 60 minutes.

With respect to cellular differentiation, cellular migration and cellular proliferation, it was determined that each was promoted under conditions in which fluorapatite concentration in the cellular environment average between 0.01 ppm and 7.00 pm, as such concentrations are given herein. For example, the concentration of fluorapatite in the cellular environment may reach a concentration averaging at least 0.01 ppm, 0.05 ppm, 0.1 ppm, 0.5 ppm, 1.00 ppm, 1.10 ppm, 1.20 ppm, 1.30 ppm, 1.40 ppm, 1.50 ppm, 1.60 ppm, 1.70 ppm, 1.80 ppm, 1.90 ppm, 2.00 ppm, 2.50 ppm, 3.00 ppm, 3.50 ppm, 4.00 ppm, 4.50 ppm, 5.00 ppm, 5.50 ppm, 6.00 ppm, 6.50 ppm, or 7.00 ppm fluorapatite after treatment with fluorapatite nano-crystalline coated hydroxylapatite. For example, the concentration of fluorapatite in the cellular environment may reach a concentration of at least 1.00 ppm fluorapatite after treatment with fluorapatite nano-crystalline coated hydroxylapatite. In some embodiments, the concentration of fluorapatite in the cellular environment may reach a concentration averaging no more than 7.00 ppm, 6.50 ppm, 6.00 ppm, 5.50 ppm, 5.00 ppm, 4.50 ppm, 4.00 ppm, 3.50 ppm, 3.00 ppm, 2.50 ppm, 2.00 ppm, 1.90 ppm, 1.80 ppm, 1.70 ppm, 1.60 ppm, 1.50 ppm, 1.40 ppm, 1.30 ppm, 1.20 ppm, 1.10 ppm, 1.00 ppm, 0.5 ppm, 0.1 ppm, 0.05 ppm, or 0.01 ppm fluorapatite after treatment with fluorapatite nano-crystalline coated hydroxylapatite. For example, the concentration of fluorapatite in the cellular environment may reach a concentration averaging 1.00 ppm to 2.00 ppm fluorapatite by 48-hours, after treatment with fluorapatite nano-crystalline coated hydroxylapatite.

A combination of the foregoing may be used to describe the concentration of fluorapatite in the cellular environment after treatment with fluorapatite nano-crystalline coated hydroxylapatite. For example, in some embodiments, the concentration of fluorapatite in the cellular environment may reach a concentration averaging at least 0.1 ppm and no more than 5.00 ppm, such as a concentration averaging at least 0.5 ppm and no more than 2.5 ppm, including a concentration averaging at least 1.00 ppm and no more than 2.00 ppm fluorapatite after treatment with fluorapatite nano-crystalline coated hydroxylapatite. In another non-limiting example, the concentration of fluorapatite in the cellular environment may reach a concentration of 1.25±0.05 ppm fluorapatite in 30 minutes, 1.57±0.12 ppm fluorapatite in 1440 minutes (24 hours), and/or 1.73±0.15 ppm fluorapatite in 2880 minutes (48 hours) and up to 4 or 8 weeks 95%±5% of the material is resorbed.

In some embodiment, cellular differentiation reaches a steady state, at fluorapatite concentrations between 0.01 ppm and 1.0 ppm, in a cellular environment. In some embodiments, cellular differentiation reaches a steady state, at fluorapatite concentrations between 1.0 ppm and 2.0 ppm fluorapatite concentration, in a cellular environment. In some embodiments, cellular differentiation reaches a steady state, at fluorapatite concentrations between 2.0 ppm and 5.0 ppm fluorapatite concentration, in a cellular environment. In some embodiments, cellular differentiation reaches a steady state, at fluorapatite concentrations between 5.0 ppm and 7.0 ppm fluorapatite concentration, in a cellular environment.

Osteoblast Differentiation (Measurement of Alkaline Phosphatase Activity)

FIG. 6 provides effects of released fluorapatite on alkaline phosphate activity in MG-63 cells. Alkaline phosphatase activity was measured after 1-week culture in the medium with diluted, low concentration of fluorapatite, 0.5, 1.0 and 2.0 ppm. Alkaline phosphatase activity was significantly higher with medium containing 1.0 ppm with the fluorapatite from the nano-crystalline surface technology, than with control medium. * P<0.05

Consistent with the cell proliferation and in vitro cell migration, alkaline phosphatase activity, a biochemical marker for early osteoblast differentiation, was promoted in the fluorapatite elution medium in comparison to the control. Although it was significantly greater at 1.0 ppm fluorapatite (p<0.05), the increase was not significant at 2.0 ppm fluorapatite.

With respect to cellular differentiation, it was determined that cellular differentiation was significantly promoted under conditions in which fluorapatite concentration in the cellular environment was between 0.01 and 7.00 ppm, as such concentrations are given herein. Indeed, promotion of cellular differentiation was observed at concentrations between 1.0 and 2.0 ppm fluorapatite, and significantly between 1.25 and 1.73 ppm. For example, in experiments with MG-63 cells, alkaline phosphatase activity after 1-week of exposure was significantly higher at 1.0 ppm fluorapatite. Alkaline phosphatase activity after 1-week of exposure at higher concentrations of fluorapatite (e.g., 2.0 ppm) was more variable. It should be noted that elevated alkaline phosphatase indicates that there is active bone formation occurring, as alkaline phosphatase is evidenced as a byproduct of osteoblast activity.

Cell Migration (Invasion Assay)

Figures 3A, 3B:
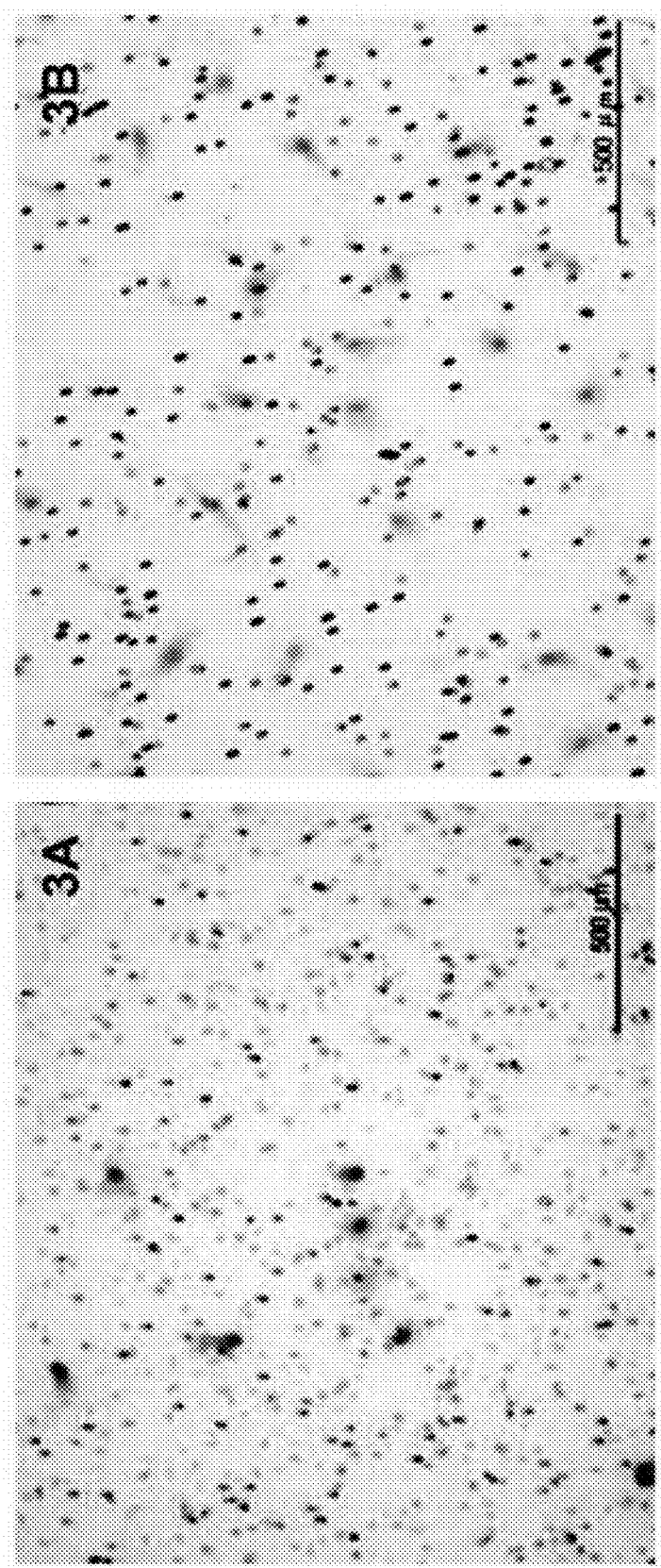
FIG. 3A shows cellular proliferation of 5-7 MG-63 human osteoblast cells that were treated with hydroxylapatite, lacking the fluorapatite nano-crystalline coating (i.e. the "control" chamber).
FIG. 3B shows cellular proliferation improved by 300%, of the MG-63 human osteoblast that were treated with the novel bone graft of the present invention (hydroxylapatite crystal comprising the fluorapatite nano-crystalline coating) (i.e. the "experimental" chamber).

To determine whether the concentration of fluorapatite would affect the cell migration in vitro, migrating live MG-63 human osteoblast cells were stained with hematoxylin and eosin stain ("H-E stain") following culture for 24 hours. Numbers of MG-63 human osteoblast cells, which migrated to the outer layer of the chamber, were counted after a 24 hour incubation period. FIG. 3A shows the control chamber where cells were treated with non-fluoridated non-ceramic synthetic bioactive resorbable hydroxylapatite, and FIG. 3B shows the experimental chamber where cells were treated with the inventive fluorapatite nano-crystalline coated hydroxylapatite bone graft. In FIG. 3A, non-treated crystals do not possess the fluorapatite nano-crystalline surface technology, demonstrating 5 to 7 osteoblast cell migration (red dots) in a field of 2.34 $mm^2$. In FIG. 3B, over 300% osteoblast cell improvement and proliferation is shown by the crystals treated with fluorapatite nano-crystalline surface technology, to generate new bone formation, with a fluorapatite concentration of 1.51±0.10 ppm, after 24 hour incubation. As shown graphically, in FIG. 4, the number of MG-63 cells counted per field of view (2.34 $mm^2$) was approximately 5 to 7 cells for the control, non-treated non-ceramic hydroxylapatite, and 18 to 20 cells for the experiment, hydroxylapatite coated with fluorapatite nano-crystalline surface technology. Therefore, the number of MG-63 cells was significantly greater after treatment with fluorapatite nano-crystalline coated hydroxylapatite as compared to non-treated hydroxylapatite, thus confirming the benefit of migration of MG-63 cells towards the released fluorapatite into the cellular environment. As demonstrated in FIG. 3B, MG-63 cells showed good spreading and motility (movement) with statistical significance and an improvement of approximately 300% of cell proliferation to lay down new bone formation, as noted in FIGS. 7 and 8 by histologic evaluation. The effect on MG-63 cell migration of fluorapatite released from fluorapatite nano-crystalline coating from the surface of the hydroxylapatite was thus clear; due to the material's potency for bone regeneration, using the fluorapatite nano-crystalline surface technology of the inventive fluorapatite nano-crystalline coating. It should be noted that even the non-ceramic hydroxylapatite without fluoridation (as the control) demonstrated a cellular proliferation by the osteoblast cell migration (in the range of 5 to 7 osteoblast cells in the field of view) due to the chemotactic bioactive nature of the underlying hydroxylapatite crystals.

With respect to cellular migration, it was determined that cellular migration was promoted under conditions in which fluorapatite concentration in the cellular environment averaging between 0.01 ppm and 7.00 μm, as such concentrations are given herein. Indeed, optimal promotion of cellular migration was observed at concentrations between 1.0 and 2.0 ppm fluorapatite.

Cell Recruitment and Proliferation (MTS Assay)

To analyze the effect of fluorapatite on cell proliferation, an MTS (MTS=[3-(4,5-dimethylthiazol-2-yl)-5-(3-carboxymethoxyphenyl)-2-(4-sulfophenyl)-2H-tetrazolium]) assay was performed with MG-63 cells. Cell proliferation after 24 hours was the highest at fluorapatite concentrations of 1.0 and 2.0 ppm ($p<0.05$), and cell proliferation continued to decrease gradually with the lowest at a fluorapatite concentration of 5.0 ppm ($p<0.005$) with continued benefit. Fluorapatite at concentrations in the range of 1.0-2.0 ppm thus promoted MG-63 cell proliferation and cell recruitment. FIG. 5 graphically provides effects of released fluorapatite on MG-63 osteoblast cell proliferation. Cell proliferation was assessed by the MTS assay, as described in Materials and Methods herein below. Differences in MG-63 osteoblast cells after 24 hours incubation with the control, non-ceramic hydroxylapatite medium were set at 100% for osteoblast cell proliferation. The comparative experiment was in the culture medium with released fluorapatite, in concentrations of 0.5 ppm, 1.0 ppm, 2.0 ppm and 5.0 ppm, where cell proliferation was highest at 1.0 ppm with a 20% improvement above the control, slightly decreased at 2.0 ppm to 16%, and was lower than the controls at 5.0 ppm by 16%.

With respect to cellular proliferation, it was determined that cellular proliferation was promoted under conditions in which fluorapatite concentration in the cellular environment averaging between 0.01 ppm and 5.00 pm, as such concentrations are given herein. It was determined that cellular proliferation was significantly promoted under conditions in which fluorapatite concentration in the cellular environment averaged between 1.00 ppm and 2.00 ppm, and most significantly promoted under conditions in which fluorapatite concentration in the cellular environment averaged between 1.25 ppm and 1.73 ppm. For example, in vitro MG-63 human like osteoblast cell proliferation was significantly promoted at a concentration of 1.25±0.05 ppm fluorapatite after 30 minutes. In another non-limiting example, MG-63 human osteoblast cell proliferation was significantly promoted at a concentration of 1.57±0.12 ppm fluorapatite after 24 hours. In yet another non-limiting example, MG-63 human osteoblast cell proliferation was significantly promoted at a concentration of 1.73±0.15 ppm fluorapatite after 48 hours.

Although it was observed that cellular proliferation was optimal at concentrations averaging between 1.0 and 2.0 ppm fluorapatite for MG-63 osteoblast. Cell proliferation was still observed at higher fluorapatite concentrations with benefit thereafter being inversely proportional to the concentration. For example, the benefit of the MG-63 osteoblast cell proliferation gradually decreased at fluorapatite concentrations higher than 2.0 ppm, and appearing less beneficial (but still having some benefit), at concentrations of fluorapatite higher than 5.0 ppm.

UTILITY

The fluorapatite nano-crystalline surface technology disclosed herein may be used in, but is not limited to, augmentation and repair of bone defects, sinus elevations, filling tooth extractions and cyst defects after enucleation (e.g., unicameral defects in orthopedics), as well as repair of periodontal bone defects, and for fortifying an implant osteotomy to secure an implant placement. Non-ceramic synthetic bioactive resorbable hydroxylapatite, the foundation of the inventive fluorapatite nano-crystalline surface technology, are physiochemically and crystallographically equivalent to human bone mineral (e.g., human trabecular bone and its crystal mineral structure), making it a pure alloplast. The spaces between the crystals and crystal clusters of the underlying hydroxylapatite are hydrophilic and facilitate cellular recruitment and tissue proliferation within the grafted material, encouraging faster cell bridging and bone restoration at the defect site. The microfine, fluorapatite nano-crystalline coating (inventive nano-crystalline surface technology) chemically bound, to a surface of the hydroxylapatite crystals and crystal clusters provides for the immediate and controlled release of low-level of fluorapatite, which, as shown herein, facilitates cell recruitment, cell differentiation, cell migration, and cell proliferation, which are biological reactions leading to osteogenesis. Furthermore, in view of the control and elimination of pathogens that proliferate and destroy bone (e.g., causing periodontitis and implantitis), the fluorapatite released from the fluorapatite nano-crystalline coated hydroxylapatite bone graft, accelerates bone restoration in a rapid formation, over two times faster than normal depending on patient's age.

EXAMPLES

The following examples are put forth so as to provide those of ordinary skill in the art with a complete disclosure and description of how to make and use the invention. The examples are not intended to limit the scope of what the inventor regards as his invention, since the scope of the present invention will be limited only by the appended claims. Efforts have been made to ensure accuracy with respect to numbers used (e.g., amounts, temperature, time, etc.) but some experimental errors and deviations should be accounted for.

Materials and Methods

Reagents and Cell Culture

Hydroxylapatite comprising fluorapatite nano-crystalline surface technology were prepared using 3.0 g of the non-ceramic synthetic bioactive resorbable hydroxylapatite (Lot no. U1201B and Lot no. X-01-01FB, Impladent Ltd., NY, USA), which was immersed in 50 ml of neutral 4% NaF solution for 3 minutes and then immediately washed twice in 200 ml of saline or filtered deionized water (American Regent Laboratories Inc., Shirley, N.Y. USA) and allowed to dry naturally (Note that in other embodiments, sterile water/usp could be used instead of saline). The control samples were non-fluoridated non-ceramic hydroxylapatite, of the same lot, immersed in distilled water for 3 minutes and examined in the same way for comparison.

Elution medium was prepared using 0.55 g of fluorapatite nano-crystalline coated hydroxylapatite immersed in 45 ml of DMEM containing no serum for 24 hours at 37° C. After immersion, the fluorapatite nano-crystalline coated hydroxylapatite is precipitated out by centrifugation at 1,500 rpm for 5 min, and the supernatant was collected. The supernatant was then filter-sterilized through a 0.2-μm pore size filter (CORNING®, USA) to yield fluorapatite elution medium. Hydroxylapatite elution medium was produced in the same manner, using a non-fluoridated control sample of hydroxylapatite. Fluorapatite concentrations in each culture medium were measured using the ion-selective electrode method (Model 96-09 Fluoride Electrode; Orion, USA). An equal amount of TISAB II (Orion) was used as total ionic strength adjustment buffer.

Human osteoblast cells, MG-63 cells, were obtained from the American Type Culture Collection (Rockville, Md., USA) and cultured in DMEM containing 10% fetal bovine serum (Sigma Aldrich, St. Louis, Mo. USA), with 5% $CO_2$ at 37° C. All assays were performed in triplicate and repeated at least three times.

Measurement of Fluorapatite Released

The concentration of fluorapatite released from fluorapatite nano-crystalline surface was measured by immersing 10 mg of fluorapatite nano-crystalline coated hydroxylapatite in 1.25 ml of Dulbecco's Modified Eagle's Medium (DMEM, Sigma-Aldrich, USA) at 37° C., and fluorapatite concentrations were determined at 0.5, 1, 2, 4, 8, 12, 24 and 48 hours after immersion.

Measurement of Alkaline Phosphatase Activity

Consistent with the cell proliferation and in vitro cell migration, alkaline phosphatase activity, a biochemical marker for early osteoblast differentiation, was promoted in the fluorapatite elution medium, in comparison to the control. In a 3.5-cm dish, $1\times10^5$ cells were seeded and when the cells reached confluence, the medium was replaced with fluoridated elution medium diluted to 0.5, 1.0, and 2.0 ppm fluorapatite. Medium containing eluted fluorapatite at each dilution was replaced every 3 days. After 1 week, cells were washed with ice-cold PBS, scraped off and collected with a rubber policeman in RIPA Lysis Buffer (Santa Cruz Biotechnology, USA) on ice. MG-63 cells were disrupted by homogenization with ultrasound for 10 seconds and kept on a rotary shaker for 30 minutes at 80 rpm under ice-cold conditions. After centrifugation for 15 minutes at 15,000 rpm, the resulting supernatant was collected for measurement. Proteins in each measurement sample were quantified using the QuickStart Protein Assay (Bio-Rad Laboratories, USA), which is a modification of the Bradford method, according to the manufacturer's protocols.

Alkaline phosphatase activity was calculated from the product concentration (nmol p-nitrophosphate/μg protein/hour) using Lab Assay ALP (Wako Pure Chemical Industries) in a Microplate Reader at 405 nm. Control activity was measured with non-fluoridated non-ceramic hydroxylapatite elution medium prepared in the same manner.

Invasion Assay

A BD BioCoat Matrigel Invasion Chamber (Becton, Dickinson and Company, USA) was used for invasion assay. Fluorapatite nano-crystalline coated hydroxylapatite (10 mg) is added to 0.75 ml of DMEM in each well of a BD Falcon Companion Plate for cell culture, and Falcon Cell Culture Inserts fitted with an 8-μm PET membrane was placed inside the wells. MG-63 cell culture (0.5 ml) with cells suspended at a density of $2.5\times10^4$ cells/well was seeded inside the cell culture inserts, followed by culture for 24 hours at 37° C. under 5% $CO_2$. The culture was then fixed with 100% methanol and stained with hematoxylin and eosin stain ("H-E stain"). The number of migrating cells (to the outer layer) was counted by photographing nine fields per well (field of view, 2.34 $mm^2$) at ×100 magnification. The concentration of fluorapatite released into the culture medium was also measured in the outer chamber using the ion selective electrode method. As a control, invasion assay was performed using non-fluoridated non-ceramic hydroxylapatite.

Cell Proliferation Assay (MTS Assay)

To analyze the effect of released fluorapatite on osteoblast cell proliferation, an MTS assay was performed with MG-63 cells. Cells were seeded at a density of $4\times10^3$ cells/well in a 96-well plate using DMEM containing serum, and cultured for 24 hours. After 24-hours incubation without serum, medium was replaced with fluorapatite elution medium diluted to final concentrations of 0.5, 1.0, 2.0, and 5.0 ppm fluorapatite. Cell proliferation was assessed following a further 24-hour period using MTS assay with CellTiter 96® AQueous One Solution Reagent (Promega, UK). Non-Ceramic hydroxylapatite elution medium was prepared in the same manner and used for the non-fluoridated control cultures.

Statistical Analysis

JMP 7.0 J (SAS Inc.) was used for statistical analysis. Student's t-test was used to compare means between two groups. The vertical bars represent +/−one standard error of the mean.

While the invention has been described and/or illustrated with respect to particular embodiments, it should be understood by those having ordinary skill in the art that the invention is not limited to the particular embodiments described and/or illustrated herein. Additional advantages and modifications of the invention will readily appear to those having ordinary skill in the art. Accordingly, it is to be understood that the description and/or the accompanying drawings as set forth herein are not intended to limit the breadth of the invention, which breadth should be inferred only from the following claims and their appropriately construed legal equivalents.

I claim:

1. A bone graft for promoting bone regeneration in a bone defect site, the bone graft comprising:
   non-ceramic hydrophilic hydroxylapatite crystals coated with a fluorapatite nano-crystalline coating, and
   non-ceramic hydrophilic hydroxylapatite crystal clusters coated with a fluorapatite nano-crystalline coating,
   wherein fluorapatite is chemically bound only to a surface of the non-ceramic hydrophilic hydroxylapatite crystals, and
   wherein fluorapatite is chemically bound only to a surface of the non-ceramic hydrophilic hydroxylapatite crystal clusters.

2. The bone graft of claim 1, wherein the non-ceramic hydrophilic hydroxylapatite crystals and the non-ceramic hydrophilic hydroxylapatite crystal clusters have physicochemical characteristics of trabecular human bone mineral, and wherein the non-ceramic hydrophilic hydroxylapatite crystals and the non-ceramic hydrophilic hydroxylapatite crystal clusters each comprise a formulation of $Ca_5(PO_4)_3(OH)$.

3. The bone graft of claim 1, wherein each of the fluorapatite nano-crystalline coating of the nonceramic hydrophilic hydroxylapatite crystals and the flourapatite nano-crystalline coating of the non-ceramic hydrophilic hydroxylapatite crystal clusters comprises a formulation of $Ca_5(PO_4)_3F$.

4. The bone graft of claim 1,
   wherein the fluorapatite nano-crystalline coated non-ceramic hydrophilic hydroxylapatite crystals are at least one of small and large,
   wherein the fluorapatite nano-crystalline coated non-ceramic hydrophilic hydroxylapatite crystal clusters are large,
   wherein small is selected from a size range of 0.001-100 μm, and
   wherein large is selected from a size range of 101-841 μm.

5. The bone graft of claim 1, wherein the fluorapatite nano-crystalline coated non-ceramic hydrophilic hydroxylapatite crystals are selected from a size range of 0.001-100 μm.

6. The bone graft of claim 1, wherein the fluorapatite nano-crystalline coated non-ceramic hydrophilic hydroxylapatite crystals and the fluorapatite nano-crystalline coated non-ceramic hydrophilic hydroxylapatite crystal clusters are selected from a size range of 100-500 μm.

7. The bone graft of claim 1, wherein the fluorapatite nano-crystalline coated non-ceramic hydrophilic hydroxylapatite crystals and fluorapatite nano-crystalline coated non-ceramic hydrophilic hydroxylapatite crystal clusters are selected from a size range of 150-841 μm.

8. The bone graft of claim 1, wherein the fluorapatite nano-crystalline coating of the fluorapatite nano-crystalline coated non-ceramic hydrophilic hydroxylapatite crystals and the fluorapatite nano-crystalline coating of the fluorapatite nano-crystalline coated non-ceramic hydrophilic hydroxylapatite crystal clusters each comprises at least one of loosely-bound fluorapatite crystallites and firmly-bound fluorapatite crystallites.

9. The bone graft of claim 8, wherein the firmly-bound fluorapatite crystallites are fluorapatites coating substantially the entire surface of the non-ceramic hydrophilic hydroxylapatite crystals and non-ceramic hydrophilic hydroxylapatite clusters; and the loosely-bound fluorapatite crystallites are scattered throughout the surface of the non-ceramic hydrophilic hydroxylapatite crystals and non-ceramic hydrophilic hydroxylapatite crystal clusters.

10. The bone graft of claim 1, wherein the bone graft is sterilized for end use.

11. The bone graft of claim 1, further comprising a binder, the bone graft comprising a dry crystal formulation.

12. The bone graft of claim 11, wherein the binder is selected from the group consisting of: polyvinylpyrrolidone; a combination of Poloxamer 407 and water; a combination of lecithin and water; a combination of glycerol and water; a combination of human collagen and water; a combination of porcine gelatin and water; a combination of calcium sulfate, carboxymethyl-cellulose, and water; and a combination of hyaluronic acid and water.

13. The bone graft of claim 12 wherein a ratio of the bone graft to the binder is between 9:1 and 8:2.

14. The bone graft of claim 1, further comprising collagen and water to form an adaptable solid shape.

15. The bone graft of claim 14, wherein a ratio of the fluorapatite nano-crystalline coated non-cermaic hydrophilic crystals and the fluorapatite nano-crystalline coated non-ceramic hydrophilic crystal clusters, the collagen, and the water is 1:1:2.

16. The bone graft of claim 1,
wherein the fluorapatite nano-crystalline coated non-ceramic hydrophilic hydroxylapatite crystals are at least one of small and large,
wherein the fluorapatite nano-crystalline coated non-ceramic hydrophilic hydroxylapatite crystal clusters are large,
wherein small is selected from a size range of 0.001-100 μm,
wherein large is selected from a size range of 101-841 μm, and
wherein a ratio of the fluorapatite nano-crystalline coated non-ceramic hydrophilic hydroxylapatite crystals comprising the non-ceramic hydrophilic small hydroxylapatite crystals to the fluorapatite nano-crystalline coated non-ceramic hydrophilic hydroxylapatite crystals comprising the large non-ceramic hydrophilic hydroxylapatite crystals and the large non-ceramic hydrophilic hydroxylapatite crystal clusters is 50:50.

17. The bone graft of claim 1,
wherein the fluorapatite nano-crystalline coated non-ceramic hydrophilic hydroxylapatite crystals are at least one of small and large,
wherein the fluorapatite nano-crystalline coated non-ceramic hydrophilic hydroxylapatite crystal clusters are large,
wherein small is selected from a size range of 0.001-100 μm,
wherein large is selected from a size range of 101-841 μm, and
wherein a ratio of the fluorapatite nano-crystalline coated non-ceramic hydrophilic hydroxylapatite crystals comprising the small non-ceramic hydrophilic hydroxylapatite crystals to the fluorapatite nano-crystalline coated non-ceramic hydrophilic hydroxylapatite crystals comprising the large non-ceramic hydrophilic hydroxylapatite crystals and the large non-ceramic hydrophilic hydroxylapatite crystal clusters is 70:30.

18. The bone graft of claim 1, wherein the non-ceramic hydrophilic hydroxylapatite crystals and the non-ceramic hydrophilic crystal clusters are intertwined to each other, thereby providing a surface volume greater than the non-ceramic hydrophilic hydroxylapatite crystals and the non-ceramic hydrophilic crystal clusters when not intertwined.

19. The bone graft of claim 1,
wherein the fluorapatite nano-crystalline coated non-ceramic hydrophilic hydroxylapatite crystals are selected from a size range of 37-100 μm,
wherein the fluorapatite nano-crystalline coated non-ceramic hydrophilic hydroxylapatite crystal clusters are selected from a size range of 101-841 μm.

20. The bone graft of claim 1, wherein the bone graft is adapted to stimulate bone regeneration by release in a time-release mechanism, when exposed to a cellular environment of a plurality of cells, fluorapatite from the fluorapatite nano-crystalline coating of the flourapatite nano-crystalline coated non-ceramic hydrophilic hydroxylapatite crystals and the nano-crystalline coating of the fluorapatite nano-crystalline coated non-ceramic hydrophilic hydroxylapatite crystal clusters.

21. The bone graft of claim 1, wherein the bone graft is adapted to release in a time-release mechanism, when exposed to a cellular environment of a plurality of cells, fluorapatite from the fluorapatite nano-crystalline coating of the flourapatite nano-crystalline coated non-ceramic hydrophilic hydroxylapatite crystals and the nano-crystalline coating of the fluorapatite nano-crystalline coated non-ceramic hydrophilic hydroxylapatite crystal clusters.

22. The bone graft of claim 1, wherein the non-ceramic hydrophilic hydroxylapatite crystals and the non-ceramic hydrophilic hydroxylapatite crystal clusters include the presence of brushite ($CaHPO_4 \cdot 2H_2O$) and monetite ($CaHPO_4$).

23. A bone graft for promoting bone regeneration in a bone defect site, the bone graft comprising:
non-ceramic hydrophilic hydroxylapatite crystals coated with a fluorapatite nano-crystalline coating, and
wherein fluorapatite is chemically bound only to a surface of the non-ceramic hydrophilic hydroxylapatite crystals.

* * * * *